US008632966B2

(12) United States Patent
Brown et al.

(10) Patent No.: US 8,632,966 B2
(45) Date of Patent: Jan. 21, 2014

(54) DETECTION OF BIOLOGICAL MOLECULES BY DIFFERENTIAL PARTITIONING OF ENZYME SUBSTRATES AND PRODUCTS

(71) Applicant: Queen's University at Kingston, Kingston (CA)

(72) Inventors: R. Stephen Brown, Kingston (CA); Samir P. Tabash, Pickering (CA); Igor S. Kozin, Kingston (CA); Eric J. P. Marcotte, Kingston (CA); Arthur N. Ley, Kingston (CA); Kevin R. Hall, Kingston (CA); Moe Hussain, Kanata (CA); Peter V. Hodson, Kingston (CA); Raymond J. Bowers, Bath (CA); Robin A. Wynne-Edwards, Kingston (CA); John G. St. Marseille, Cornwall (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 13/738,620

(22) Filed: Jan. 10, 2013

(65) Prior Publication Data

US 2013/0217041 A1    Aug. 22, 2013

Related U.S. Application Data

(60) Division of application No. 12/213,207, filed on Jun. 16, 2008, now Pat. No. 8,377,686, which is a continuation of application No. 10/665,718, filed on Sep. 22, 2003, now Pat. No. 7,402,426.

(60) Provisional application No. 60/412,015, filed on Sep. 20, 2002.

(51) Int. Cl.
*C12Q 1/00* (2006.01)
*G01N 21/64* (2006.01)

(52) U.S. Cl.
USPC .................. 435/4; 435/288.7; 435/287.9; 435/288.1; 435/288.3; 435/808; 600/317; 600/309; 422/82.07; 422/82.06

(58) Field of Classification Search
USPC ......... 435/4, 288.7, 287.9, 288.1, 288.3, 808; 600/317, 309; 422/82.07, 82.06
See application file for complete search history.

(56) References Cited

U.S. PATENT DOCUMENTS 4,974,929 A   12/1990 Curry
5,238,809 A    8/1993 Wolfbeis
(Continued)

FOREIGN PATENT DOCUMENTS

EP    0044140      1/1982
EP    1 335 200    8/2003
(Continued)

OTHER PUBLICATIONS

Alonso, J.L.; et al. "Quantitative Determination of *E. coli* and Fecal Coliforms in Water Using a Chromogenic Medium". J. Envir. Sci. Health A33(6): 1229-1248 (1998).
(Continued)

*Primary Examiner* — Nathan Bowers
(74) *Attorney, Agent, or Firm* — Stephen J. Scribner

(57) ABSTRACT

This invention relates to a method and apparatus for detecting a biological molecule associated with enzyme activity in a sample. The invention is applicable to detecting a microorganism associated with an enzyme in a sample such as water, food, soil, or a biological sample. According to a preferred embodiment of the method of the invention, a sample containing an enzyme of interest or a microorganism associated with the enzyme is combined with a suitable substrate, and a fluorescent product of the enzyme-substrate reaction is selectively detected. The fluorescent product is detected with a partitioning element or optical probe/partitioning element of the invention. In one embodiment the partitioning element provides for partitioning of only the fluorescent product molecule into the probe. The invention also provides an automated system for monitoring for biological contamination of water or other samples.

15 Claims, 21 Drawing Sheets

(56) References Cited

U.S. PATENT DOCUMENTS

| | | | |
|---|---|---|---|
| 5,364,767 | A | 11/1994 | Flowers et al. |
| 5,376,551 | A | 12/1994 | Yoshikami |
| 5,567,290 | A | 10/1996 | Vadgama et al. |
| 5,861,270 | A | 1/1999 | Nelis |
| 6,060,266 | A | 5/2000 | Naqui et al. |
| 6,566,508 | B2 | 5/2003 | Bentsen et al. |
| 6,753,186 | B2 | 6/2004 | Moskoff |
| 7,096,053 | B2 | 8/2006 | Loeb et al. |
| 7,402,426 | B2 | 7/2008 | Brown et al. |
| 8,377,686 | B2 | 2/2013 | Brown et al. |
| 2003/0222012 | A1 | 12/2003 | Lee et al. |
| 2003/0228681 | A1 | 12/2003 | Ritts et al. |
| 2004/0047535 | A1 | 3/2004 | Ukrainczyk |

FOREIGN PATENT DOCUMENTS

| | | |
|---|---|---|
| GB | 2 078 370 | 1/1982 |
| JP | 57-030952 | 2/1982 |
| JP | 63-247646 | 10/1988 |
| JP | 64-63842 | 3/1989 |
| JP | 3065639 | 3/1991 |
| JP | 04-330298 | 11/1992 |
| JP | 07-151725 | 6/1995 |
| WO | 9216648 | 10/1992 |
| WO | 9303051 | 2/1993 |
| WO | 9932655 | 7/1999 |

OTHER PUBLICATIONS

Arkles, B. "Look What You Can Make Out of Silicones". Chemtech. 13: 542-555 (1983).

D'Auriac, M.B.A.; et al. "Field Evaluation of a Semiautomated Method for Rapid and Simple Analysis of Recreational Water Microbiological Quality". Applied and Environmental H / Microbiology 66:4401-4407 (2000).

Davies, C.M.; et al. "Rapid Enzymatic Detection of Faecal Pollution". Wat. Sci. Tech. 34(7-8):169-171 (1996).

Davies, C.M.; et al. "Field Evaluation of a Rapid Portable Test for Monitoring Fecal Coliforms in Coastal Waters". Environ. Texico/. 14: 355-359 (1999).

"European School on Sensors for Food Applications", Marciana Marina, Elba Island, Apr. 18-29, 1999, www.inapg.inra.fr/ens_rech/siab/asteq/elba/elba index.

Fischer, B.; et al. "A Novel Method for Stereoselective Glucuronidation". J.Org. Chern. 49:4988-4993 (1984).

Frampton, E.W.; et al. "Methods for *Escherichia coli* Identification in Food, Water and Clinical Samples Based on Beta-Glucuronidase Detection". J. Appl. Bacter. 74: 223-233 (1993).

Sansubrino et al. "Development of an optical fibre sensor for ammonia, urea, urease, and IgG." Biosensors & Bioelectronics 9 (1994) 207-216.

Gee, KR; et al. "Fiuorogenic Substrates Based on Fluorinated Umbelliferones for Continuous Assays of Phosphatases and B-Galactosidases". Anal. Biachem. 273: 41-48 (1999).

Hall, J.; et al. Reduction Products of the Hydroxyanthraquinones Part II. J. Chem. Sac. 123: 2029-2037 (1923).

Helferich, B.; et al. "Eine neue Methode zur Synthese von Glykosiden der Phenole". Ber. Dtsch. Chem. Ges. 66: 378-383 (1933). [In German].

Kleine, H.P.; et al. "Phase-Transfer-Catalyzed Syntheses of 2,3,4,6-tetra-0-acetyl-Beta-D-galactopyranosides". Carbo. Res. 142: 333-337 (1985).

Kiene, L.; et al. "On-line Detection of Coliforms". Water Supply. 17(2): 81-86 (1999).

Ley, A. N.; et al. "Indoxyl-Beta-D-glucuronide, a Novel Chromogenic Reagent for Specific Detection and Enumeration of *Escherichia coli* in Environmental Samples". Can. J. Microbial. 34: 690-693 (1988).

Manafi, M.; et al. "Fiuorogenic and Chromogenic Substrates Used in Bacterial Diagnostics". Microbial. Rev. 55(3): 335-348 (1991).

Marazuela, M.D.; et al. "Fiber-Optic Biosensors—An Overview". Anal. Bioanal. Chem. 372: 664-682 (2002).

Nelis, H.; et al. "Enzymatic Detection of Coliforrns and *Escherichia coli* Within 4 Hours". Water, Air, and Soil Pollution 123: 43-52 (2000).

Park, S.J. et at. "Spectrofluorometric Assay for Rapid Detection of Total and Fecal Coliforrns from Surface Water". AQPI. Enviro. Micro. 61(5): 2027-2029 (1995).

Prescott, A.; et al. "Feasibility of Fast-Response Testing for Coliform Bacteria in Distribution Systems" American Water Works Association Research Foundation, 2002.

Robertson, W .; et al. Evaluation of a Rapid Method for *E. coli* and Thermotolerant Coliforrns in Recreational Waters. Wat. Sci. Tech. 38(12): 87-90 (1998).

Stachulski, A.V.; et al. "The Synthesis of 0-glucuronides". Natural Product Reports. 173-186 (1998).

DETECTION OF BIOLOGICAL MOLECULES BY DIFFERENTIAL PARTITIONING OF ENZYME SUBSTRATES AND PRODUCTS

RELATED APPLICATIONS

This application is a division of U.S. patent application Ser. No. 12/213,207, filed Jun. 16, 2008, now U.S. Pat. No. 8,377,686, issued Feb. 19, 2013, which is a division of U.S. patent application Ser. No. 10/665,718, filed Sep. 22, 2003, now U.S. Pat. No. 7,402,426, issued Jul. 22, 2008, and claims the benefit of the filing date of U.S. Provisional Patent Application No. 60/412,015, filed Sep. 20, 2002, the contents of all of which are incorporated herein by reference in their entirety.

FIELD OF THE INVENTION

This invention relates to a method and apparatus for detecting biological molecules, such as enzymes associated with biological contaminants, in samples such as water and food products, by differential partitioning of enzyme substrates and products. In particular, this invention relates to a method and apparatus for detecting enzyme activity.

BACKGROUND OF THE INVENTION

The ability to detect biological molecules associated with enzyme activity has application in fields such as testing for biological contamination of water and food products. Of particular interest is the ability to detect biological (e.g., bacterial) contamination of water. Usually, methods for detection of bacteria such as *Escherichia coli* (*E. coli* or EC) and total coliform (TC) are based on detection of indicator enzyme activity in a broth designed to promote growth of the target organism. Accepted indicator enzymes are β-glucuronidase (β-glu) and β-galactosidase (β-gal) for EC and TC, respectively. Methods which use these enzymes rely on a reaction of the enzyme with a chromogenic or fluorogenic compound to measure the enzyme activity (for reviews, see refs. 1 and 2). In the case of β-glu or β-gal, usually a glucuronide or galactoside conjugate of a dye compound is added to the sample broth as a substrate, and if the target enzymes are present, the conjugate is converted to a free dye molecule. The enzyme-dependent conversion is detected by a change in colour or fluorescence of the free dye molecule compared to the conjugate. Some tests use soluble products detected in solution, with the coliform cells usually also suspended in solution. Others use coliform cells on the surface of a filter, membrane, or gel, usually with an insoluble dye product which adsorbs onto the support to form a coloured or fluorescent spot around colonies of target organisms (3). Some supported formats use multiple dye substrates which produce a variety of colours depending on which organisms are present.

However, the above approaches are vulnerable to sources of error, such as suitability of broth and incubation conditions for all target coliform types, as well as presence of non-target organisms which may contribute to the indicator enzyme activity. Nonetheless, the reliability of established methods is high enough that there is broad regulatory acceptance of these methods for assessment of samples ranging from meat products to drinking water.

Further, in routine or commercial uses of such substrates, detection is usually done visually by human eye, which presents significant limitations in performance. A large number of coliform cells must be present before enough substrate will be converted for the product to be visible. This requires significant incubation and growth for detection of a small initial number of cells, and a standard 100 mL sample is incubated for 24 h to provide a detection limit of one coliform cell in the initial sample. In some cases, more rapid detection is reported, but normally only with a higher detection limited accepted (e.g., 100 to 300 cells in a 100 mL sample (4,5,6)). Also, visual detection is not quantitative, and these tests are normally used in a "presence/absence" mode where the actual number of coliform cells is not determined. An exception to the latter is some plating methods, where the number of colonies is counted and therefore the number of cells in the sample quantitatively determined (3). This, however, is a very labour-intensive, time-consuming process which also requires long incubation, and has limited dynamic range.

SUMMARY OF THE INVENTION

According to one aspect of the invention there is provided a method for detecting a biological molecule associated with activity of at least one enzyme in a sample, comprising: combining at least one enzyme with at least one substrate under conditions which allow for the enzyme to react with the substrate; providing a partitioning element for partitioning of said biological molecule thereinto; and detecting fluorescence of said biological molecule in said partitioning element; wherein said fluorescence is indicative of activity of said enzyme.

In one embodiment, said partitioning element comprises an optical probe. In another embodiment, said partitioning element comprises a polymer film, such as polydimethylsiloxane (PDMS). In a preferred embodiment, said conditions which allow for the enzyme to react with the substrate comprise aqueous conditions.

In one embodiment, the biological molecule is the substrate and said detecting fluorescence comprises detecting a change in amount of fluorescence. In a preferred embodiment, the biological molecule is a product of the enzyme-substrate reaction.

In one embodiment, the enzyme activity is associated with a microorganism. In a preferred embodiment, the microorganism is a biological contaminant. In another embodiment the at least one enzyme is selected from β-glucuronidase and β-galactosidase. In a preferred embodiment, the microorganism is selected from *E. coli* and total coliform. In various embodiments the at least one substrate is selected from pyrene-β-D-glucuronide, anthracene-β-D-glucuronide, pyrromethene-β-D-glucuronide, pyrene-β-D-galactopyranoside, and anthracene-β-D-galactopyranoside, and the enzyme activity is detected in a sample selected from water, a biological sample, food, and soil.

In one embodiment, said enzyme and substrate are combined in a cartridge comprising said partitioning element.

In accordance with a second aspect of the invention there is provided a method for detecting a biological contaminant in a sample, comprising: combining the sample with at least one substrate under conditions which allow for an enzyme associated with the biological contaminant to react with the substrate; and detecting fluorescence of a product of the enzyme-substrate reaction; wherein said fluorescence is indicative of said biological contaminant in the sample.

In various embodiments the sample is selected from water, a biological sample, food, and soil. In a preferred embodiment said fluorescence of a product of the enzyme-substrate reaction is detected by partitioning of the product into an optical probe.

In one embodiment said conditions which allow for the enzyme to react with the substrate comprise aqueous conditions. In another embodiment said enzyme is at least one of β-glucuronidase and β-galactosidase. In a further embodiment said microorganism is selected from *E. coli* and total coliform. In further embodiments, said at least one substrate is selected from pyrene-β-D-glucuronide, anthracene-β-D-glucuronide, pyrromethene-β-D-glucuronide, and pyrene-β-D-galactopyranoside.

In accordance with a third aspect of the invention there is provided an optical probe for detecting fluorescence of a molecule, comprising: an optical waveguide; and a partitioning element disposed on one end of the optical waveguide; wherein said fluorescent molecule is selectively partitioned into the partitioning element, such that said fluorescence is coupled into the waveguide.

In one embodiment the fluorescent molecule is selected from an enzyme substrate and a product of an enzyme-substrate reaction. In another embodiment the partitioning element is a polymer film. In a preferred embodiment the polymer film comprises polydimethylsiloxane (PDMS). In another embodiment the optical probe further comprises a spectrometer for measuring said fluorescence.

In accordance with a fourth aspect of the invention there is provided an apparatus for detecting fluorescence of a molecule, comprising: an optical probe as described above; an excitation light source; and a spectrometer for measuring fluorescence of said molecule; wherein said fluorescence is indicative of said molecule.

In a preferred embodiment, the fluorescent molecule is selected from an enzyme substrate and a product of an enzyme-substrate reaction. In one embodiment said enzyme is associated with a microorganism. In various embodiments said enzyme is selected from β-glucuronidase and β-galactosidase. In further embodiments said microorganism is selected from *E. coli* and total coliform. In various embodiments said substrate is selected from pyrene-β-D-glucuronide, anthracene-β-D-glucuronide, pyrromethene-β-D-glucuronide, and pyrene-β-D-galactopyranoside.

In accordance with another aspect of the invention there is provided an automated system for detecting a biological contaminant in a sample, comprising: a sample incubator for incubating the sample with at least one substrate under conditions which allow for an enzyme associated with a microorganism to react with the substrate; an apparatus as described above for detecting fluorescence of a product of the enzyme-substrate reaction; and a control unit for controlling operation of said system and for storing and outputting data relating to said detection of fluorescence; wherein said detected fluorescence is indicative of said biological contaminant in the sample.

In one embodiment, the system further comprises a communications unit for relaying data relating to biological contamination of the sample. In various embodiments the sample is selected from water, a biological sample, food, and soil. In a preferred embodiment, said conditions which allow for the enzyme to react with the substrate comprise aqueous conditions. In further embodiments said enzyme is selected from β-glucuronidase and β-galactosidase, and said microorganism is selected from *E. coli* and total coliform. In various embodiments said at least one substrate is selected from pyrene-β-D-glucuronide, anthracene-β-D-glucuronide, pyrromethene-β-D-glucuronide, and pyrene-β-D-galactopyranoside.

In accordance with another aspect of the invention there is provided a kit for detecting a biological contaminant in a sample, comprising: an apparatus as described above; a substrate for an enzyme associated with the biological contaminant; and an incubator for incubating the sample and the substrate; wherein the kit provides an indication of said biological contaminant in the sample.

In various embodiments the sample is selected from water, food, a biological sample, and soil. In a preferred embodiment the biological contaminant is at least one microorganism selected from *E. coli* and total coliform.

In one embodiment the enzyme is at least one enzyme selected from β-glucuronidase and β-galatosidase. In a further embodiment the substrate is at least one substrate selected from pyrene-β-D-glucuronide, anthracene-β-D-glucuronide, pyrromethene-β-D-glucuronide, and pyrene-β-D-galactopyranoside.

According to another aspect of the invention there is provided an optical probe for detecting fluorescence of a molecule, comprising: an optical waveguide; and a partitioning element disposed on one end of the optical waveguide; wherein said molecule is selectively partitioned into the partitioning element, such that fluorescence of the molecule is coupled into the waveguide.

In one embodiment, the fluorescent molecule is selected from an enzyme substrate and a product of an enzyme-substrate reaction. In another embodiment, the partitioning element is a polymer film. In a preferred embodiment, the polymer film comprises polydimethylsiloxane (PDMS). In another embodiment, the optical waveguide is an optical fiber.

According to another aspect of the invention there is provided an apparatus for detecting presence of a molecule, comprising: the optical probe described above; an excitation light source; and a detector for detecting fluorescence of said molecule; wherein said detected fluorescence is indicative of presence of said molecule.

In one embodiment, the fluorescent molecule is selected from an enzyme substrate and a product of an enzyme-substrate reaction. In another embodiment, said enzyme is associated with a microorganism. In a further embodiment, said enzyme is selected from β-glucuronidase and β-galactosidase.

In one embodiment, said microorganism is selected from *E. coli* and total coliform. In another embodiment, said substrate is selected from pyrene-β-D-glucuronide, anthracene-β-D-glucuronide, pyrromethene-β-D-glucuronide, pyrene-β-D-galactopyranoside, and anthracene-β-D-galactopyranoside.

According to another aspect of the invention there is provided a system for detecting a biological molecule associated with activity of at least one enzyme in a sample, comprising: a vessel for incubating the sample and at least one substrate such that the enzyme to reacts with the substrate to produce said biological molecule; a partitioning element that allows partitioning of said biological molecule thereinto; an excitation light source that irradiates said biological molecule partitioned into said partitioning element; a detector that detects fluorescence of said biological molecule partitioned into said partitioning element; and a control unit; wherein said detected fluorescence is indicative of activity of said enzyme in the sample.

In one embodiment, the control unit performs at least one function selected from controlling operation of said system, storing data relating to fluorescence detection, and outputting data relating to fluorescence detection. In another embodiment, the vessel comprises a removable cartridge for containing the sample and the substrate.

In another embodiment, said partitioning element is disposed in said removable cartridge. In a further embodiment, said system comprises a communications unit that relays data relating to fluorescence detection to a communications network. In another embodiment, said enzyme is associated with a biological contaminant. In a further embodiment, the sample is selected from water, a biological sample, food, and soil. In another embodiment, the enzyme is selected from β-glucuronidase and β-galactosidase, and said biological contaminant is selected from E. coli and total coliform. In various embodiments, said at least one substrate is selected from pyrene-β-D-glucuronide, anthracene-β-D-glucuronide, pyrromethene-β-D-glucuronide, pyrene-β-D-galactopyranoside, and anthracene-β-D-galactopyranoside. In another embodiment, the system further comprises means to calibrate said partitioning element and optical components of the system or to monitor said fluorescence detection, or both.

In one embodiment, said means to calibrate said partitioning element and to monitor said fluorescence detection comprises: a fluorophore that partitions into said partitioning element and fluoresces at a different wavelength than said biological molecule; wherein said fluorescence of said fluorophore is detected by the detector; and wherein said control unit uses the detected fluorescence to calibrate the partitioning element and optical components of the system or to monitor fluorescence detection of the system.

According to another aspect of the invention there is provided a kit for detecting a biological contaminant in a sample, comprising: the apparatus described above; and a substrate for an enzyme associated with said biological contaminant; wherein the kit provides an indication of the presence or amount of said biological contaminant in the sample.

In another embodiment, the kit further comprises a vessel for incubating the sample and the substrate. In one embodiment, the sample is selected from water, food, a biological sample, and soil. In another embodiment, said biological contaminant is at least one microorganism selected from E. coli and total coliform. In another embodiment, the enzyme is at least one enzyme selected from β-glucuronidase and β-galactosidase. In another embodiment, the substrate is at least one substrate selected from pyrene-β-D-glucuronide, anthracene-β-D-glucuronide, pyrromethene-β-D-glucuronide, pyrene-β-D-galactopyranoside, and anthracene-β-D-galactopyranoside.

According to another aspect of the invention there is provided a method for detecting a target species, comprising: combining an antibody that is specific for said target species with a sample under conditions which allow the antibody to bind the target species; providing an enzyme which allows quantification of said bound antibody by producing a fluorescent molecule; providing a partitioning element for partitioning of said fluorescent molecule thereinto; and detecting fluorescence of said fluorescent molecule in said partitioning element; wherein said detected fluorescence is indicative of activity of said enzyme in the sample.

In one embodiment, said antibody is conjugated to said enzyme. In another embodiment, said enzyme is conjugated to a second antibody that is specific to the antibody that is specific for the target species and the conjugate is mixed with the combination of the antibody specific for the target species and the sample. In another embodiment, fluorescence is detected continuously throughout the enzyme-substrate reaction. In another embodiment, fluorescence is detected after a set time during the enzyme-substrate reaction. In a further embodiment, the target species is a biological or chemical contaminant. In another embodiment, the target species is selected from the group consisting of bacteria, protozoa and viruses.

BRIEF DESCRIPTION OF THE DRAWINGS

The invention will now be described, by way of example, with reference to the accompanying drawings, wherein:

FIGS. 11A to 11D are plots illustrating kinetic models for time to detection of E. coli or total coliform using a substrate and an optical probe according to the invention, wherein FIG. 11A shows E. coli detection time at various initial cell counts with a pyrene-β-D-glucuronide substrate;

FIG. 11B shows E. coli detection time at various initial cell counts with a anthracene-β-D-glucuronide substrate;

FIG. 11C shows total coliform detection time at various cell counts using a pyrene-β-D-galactopyranoside substrate; and FIG. 11D shows total coliform detection time at various cell counts using a anthracenyl-β-D-galactopyranoside substrate;

DETAILED DESCRIPTION OF THE INVENTION

Figure 1:
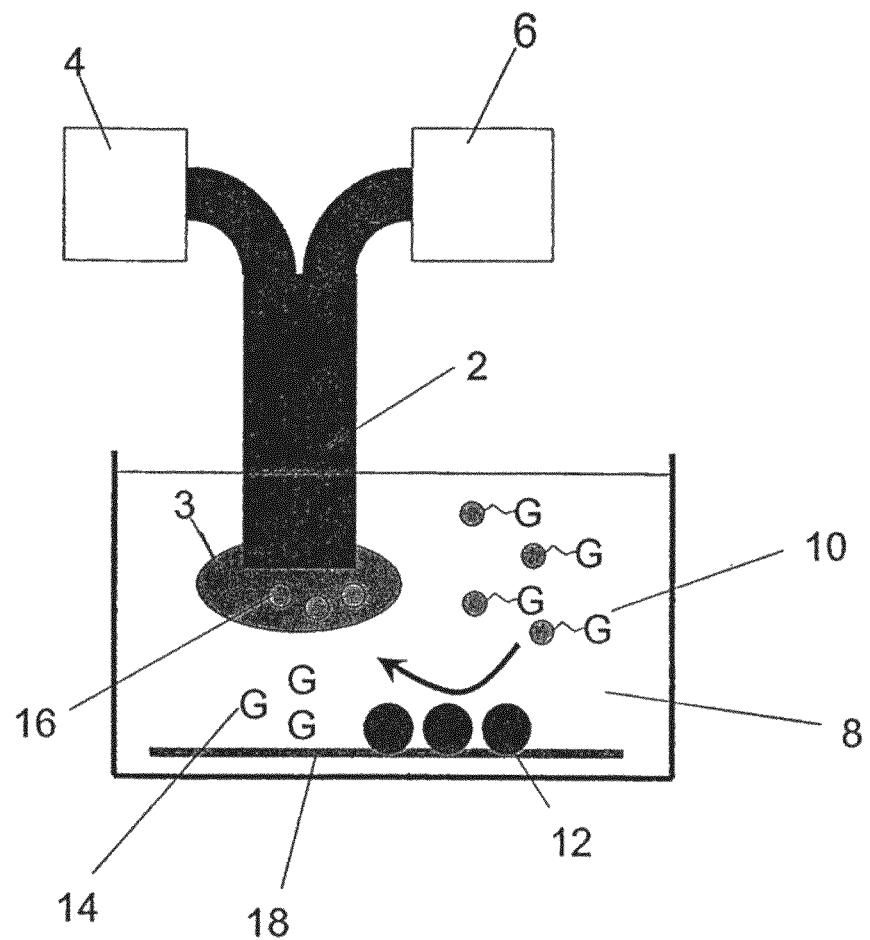
FIG. 1 shows a scheme for optical probe detection of enzyme activity according to the invention.

According to a broad aspect of the invention, there is provided a method and apparatus for reliable and rapid detection of biological molecules associated with enzyme activity. The invention is applicable to the detection of biological molecules associated with enzyme activity of biological contaminants, such as microorganisms. One practical application of the invention therefore relates to the detection of biological contaminants in samples such as water and food, where rapid detection is critical to preventing the spread of contamination and infection of individuals through consumption of contaminated water or food. Another practical application of the invention is use in assays, such as enzyme-linked immunosorbent assay (ELISA), for determination of enzyme labels.

As used herein, the term "biological molecule" is intended to refer to any molecule which can function as a substrate of an enzymatic reaction, or any molecule that can be produced by an enzymatic reaction, regardless of whether the molecule is found in nature. Rather, the molecule is termed "biological" because either (a) it is effective to bind to and be metabolized by an enzyme, or (b) it is effectively produced by enzymatic catalysis. Thus, synthetic substrates and their products are termed "biological" for the purposes of this disclosure.

In particular, the invention provides for reliable and rapid detection of enzyme activity. According to the invention, target enzyme activity is detected by providing to an enzyme a substrate comprising a fluorophore, and selectively detecting fluorescence of a fluorescent product of the enzyme-substrate reaction at a very low product concentration. Alternatively, target enzyme activity is detected by providing to an enzyme a substrate comprising a fluorophore, and selectively detecting fluorescence of the substrate and its rate of decrease as the enzyme-substrate reaction proceeds. Selective detection of the fluorescent product or substrate is achieved by providing an optical probe having a partitioning element, or simply a partitioning element, wherein the product or substrate is partitioned into the partitioning element. The optical probe having a partitioning element, or partitioning element, are optically coupled to suitable optical hardware for detecting fluorescence of the product or substrate partitioned into the partitioning element.

The ability to detect a product of the enzyme-substrate interaction at a very low product concentration or a minute change in substrate concentration translates into rapid detection because of the short time required to produce only a small amount of the product, or remove a small amount of substrate. In embodiments in which the presence of microorganisms is detected, therefore, only a small number of microorganisms, and hence a short incubation period, is required for detection. While the invention will be described primarily with respect to the detection of enzyme-substrate product, it will be understood that the invention is equally applicable to the detection of substrate.

Detection of enzyme activity according to the invention can be carried out in any medium where target enzymes are active, and which is sufficiently fluid to allow for partitioning of a molecule of interest, such as a product of the enzyme-substrate reaction, into the partitioning element. Suitable media are aqueous, and may be fluids (e.g., liquids) or semi-solids (e.g., biological tissues, gels). Generally, the invention is used to detect a target enzyme in a sample, such as, for example, water, food, biological samples such as tissues and bodily fluids, and soil. Analysis of some samples, such as certain food, biological, and soil samples, requires that the sample be combined with a suitable medium.

As used herein, the terms "detection" or "detecting" and "monitoring" are interchangeable and are intended to mean detecting enzyme activity and/or the presence of microorganisms either on a one-off basis (e.g., a discrete sample), or a continuous basis (e.g., continuous sampling at regular or random intervals).

To optimize an enzyme activity detection scheme for rapid detection, three criteria should be met:
1) The substrate should react with the target enzyme with a high rate constant.
2) The product should be highly fluorescent such that a trace quantity is easily detected.
3) There should be a large difference in fluorescence between the substrate and the product so that a fluorescence signal from the solution changes upon enzyme conversion.

These criteria place significant constraints on the optimization of conventional detection schemes. For example, because a fluorescence change is required, it is possible that a given substrate may not be optimum in terms of rate of conversion by the enzyme or detection limit of the product. Also, fluorogenic candidates which may be better substrates for an enzyme or have a very fluorescent product may not be appropriate if the substrate itself fluoresces, preventing detection of conversion. The invention overcomes such constraints.

Many of the lowest reported detection limits for fluorophores involve polycyclic aromatic hydrocarbons, fluorescein derivatives, rhodamine derivatives, or organometallic compounds such as chelated lanthanides. Such fluorophores have not been used in substrates for detecting β-glucuronidase (glu) or β-galactosidase (gal) activity in conventional detection schemes, because derivatives with the corresponding sugars (glucuronide and galactoside) having significantly different fluorescence spectra or intensities relative to the product are unknown. Instead, the fluorophores currently used are almost all coumarin derivatives, such as umbelliferone, which have acceptable fluorescence intensity but much lower fluorescence as a conjugate with glucuronide or galactoside. In contrast, the invention permits the use of a much wider range of fluorophores in substrates.

A wide variety of substrates has been reported, many of which are used in commercial detection applications. For detection of conversion product in solution, fluorogenic dyes are preferred. For example, conjugates of umbelliferone and umbelliferone derivatives (e.g., 4-methylumbelliferone, trifluoromethylumbelliferone (7)) are favoured because of good contrast in fluorescence between the product and the substrate, as well as rapid kinetics for reaction of conjugates with either the β-glu or β-gal enzymes. Other substrates such as dioxetane (8), have also been reported. Chromogenic substrates have been used in soluble detection schemes, but tend to be favoured for use in membrane or gel-supported cell detection. Examples include indolyl (9) and indoxyl conjugates (10).

According to one aspect of the invention, there is provided a method of detecting biological molecules associated with enzyme activity in a sample. As used herein, the term "biological molecule" is intended to mean an enzyme substrate or any product of an enzyme-substrate reaction. The method comprises combining a target enzyme or a biological contaminant associated with the target enzyme and a substrate, irradiating the combination with excitation light (i.e., light of a wavelength which produces fluorescence in either or both the substrate and product), and selectively detecting fluorescence of either the substrate or any product of the enzyme-substrate reaction. Preferably, fluorescence of a fluorescent product of the enzyme-substrate reaction is detected. Where the sample is not substantially a liquid or semi-liquid (e.g., a gel), it is preferable that the substrate and sample are combined in a solution. Suitable solutions include any solution which can support and/or promote enzyme activity. Where cells are employed, a suitable solution may be, for example, an appropriate medium (i.e., "broth") selected to support and promote growth of the cells under investigation. For cells and most enzymes, such solutions are aqueous. The product of the enzyme-substrate reaction can be, for example, a free fluorescent (dye) molecule, the fluorescence of which is detected.

According to the invention, fluorescence is detected by an optical probe which distinguishes between the product and the substrate, such that only fluorescence of the product or the substrate is detected. In particular, fluorescence of either the product or the substrate is detected by providing a partitioning element, alone or associated with an optical probe, that allows for partitioning of either the product or the substrate therein. When connected to a suitable device for measuring fluorescence (i.e., light), such as, for example, a spectrometer or a filter photometer, the partitioning element/optical probe produces a signal having a magnitude which varies predictably (e.g., linearly) with the intensity of the fluorescence, which is a function of the product or substrate concentration. In a preferred embodiment, the combination of substrate, product, and partitioning element is chosen such that the substrate is not detected and the product is detected at the lowest possible concentration. Thus, by distinguishing between fluorescence of the product and the substrate, the third optimization criterion referred to above is overcome.

It will be appreciated that the invention can be applied to detection of activity of any enzyme, provided that (1) a substrate for such target enzyme can be conjugated with a fluorophore, (2) the target enzyme-substrate reaction produces a fluorescent product, and (3) the fluorescent product can be selectively detected with a partitioning element/optical probe of the invention. For enzymes which cleave chemical bonds, the substrate must contain a moiety which binds to the enzyme, and be conjugated to the fluorescent product through a bond which the enzyme will cleave. For other enzyme reactions, such as some peroxidase reactions in which there is only chemical conversion of the substrate to give the product; suitable substrates are those which provide for the product being partitioned into the partitioning element.

It will be appreciated that the invention can be used to detect the presence of more than one enzyme, which may correspond to more than one species or strain of microorganism, simultaneously. This requires the use of a substrate suitable for each enzyme under consideration. If the fluorescent products of each different enzyme-substrate reaction fluoresce at different wavelengths, then activity of each enzyme under consideration can be detected. Alternatively, if the fluorescent products of each different enzyme-substrate reaction fluoresce at the same wavelength, then activity of at least one of the enzymes can be detected.

In preferred embodiments, enzymes to which the invention is directed are β-glucuronidase (glu) and β-galactosidase (gal). In such embodiments the invention provides a method for detecting the presence of *E. coli*, including its various strains (e.g., ATCC 25922; ATCC 35150 serotype O157:H7), as well as stock No. 413, *E. coli* B-type (Queen's University at Kingston, Kingston, Ontario, Canada) and sewage isolate stock Nos. KS1 and KS2 (Kingston) (see Example 6), and other microorganisms such as, for example, *Enterobacter cloacae* (ATCC 13047), *Citrobacter freundii* (ATCC 8090), *Klebsiella pneumoniae* (ATCC 13883), *Pseudomonas aeruginosa* (ATCC 27853), and total coliform, in samples such as water and food.

Suitable substrates for β-glu and β-gal are any substrates with a glucuronide or a galactoside moiety, respectively, where the term "glucuronide" is intended to include any salts and free acids thereof. Examples of suitable substrates include, but are not limited to:

pyrene-β-D-glucuronide (e.g., 1- or 2-pyrenyl-β-D-glucuronide);

anthracene-β-D-glucuronide (e.g., 1-, 2-, or 9-anthracenyl-β-D-glucuronide);

pyrromethene-β-D-glucuronide (e.g., 1-hydroxymethyl-3,5,7-trimethylpyrromethenedifluoroborate-β-D-glucuronide);

pyrene-β-D-galactopyranoside (e.g., 1- or 2-pyrenyl-β-D-galactopyranoside); and anthracene-β-D-galactopyranoside (e.g., 1-, 2-, or 9-anthracenyl-β-D-galactopyranoside).

For example, β-glu activity is detected with pyrene-β-D-glucuronide (pyr-glu), with the detected product being hydroxypyrene (HP), as shown in the reaction scheme below:

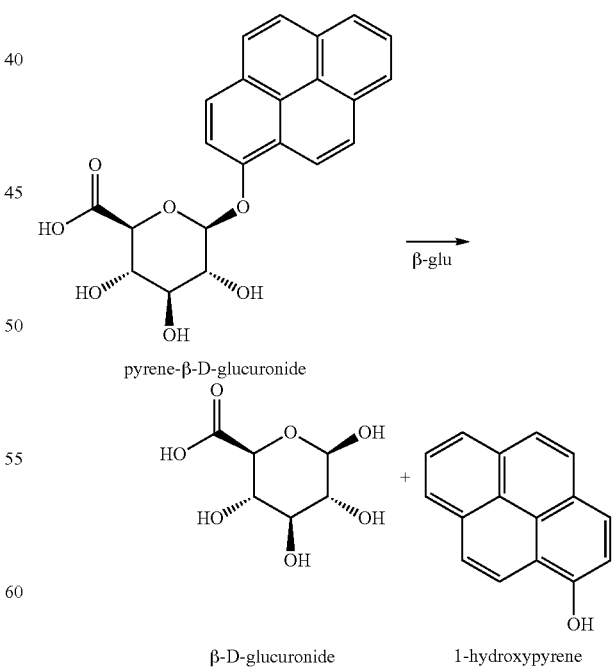

When β-glu activity is detected with anthracene-β-D-glucuronide (ant-glu), the detected product is hydroxyanthracene, as shown in the reaction scheme below:

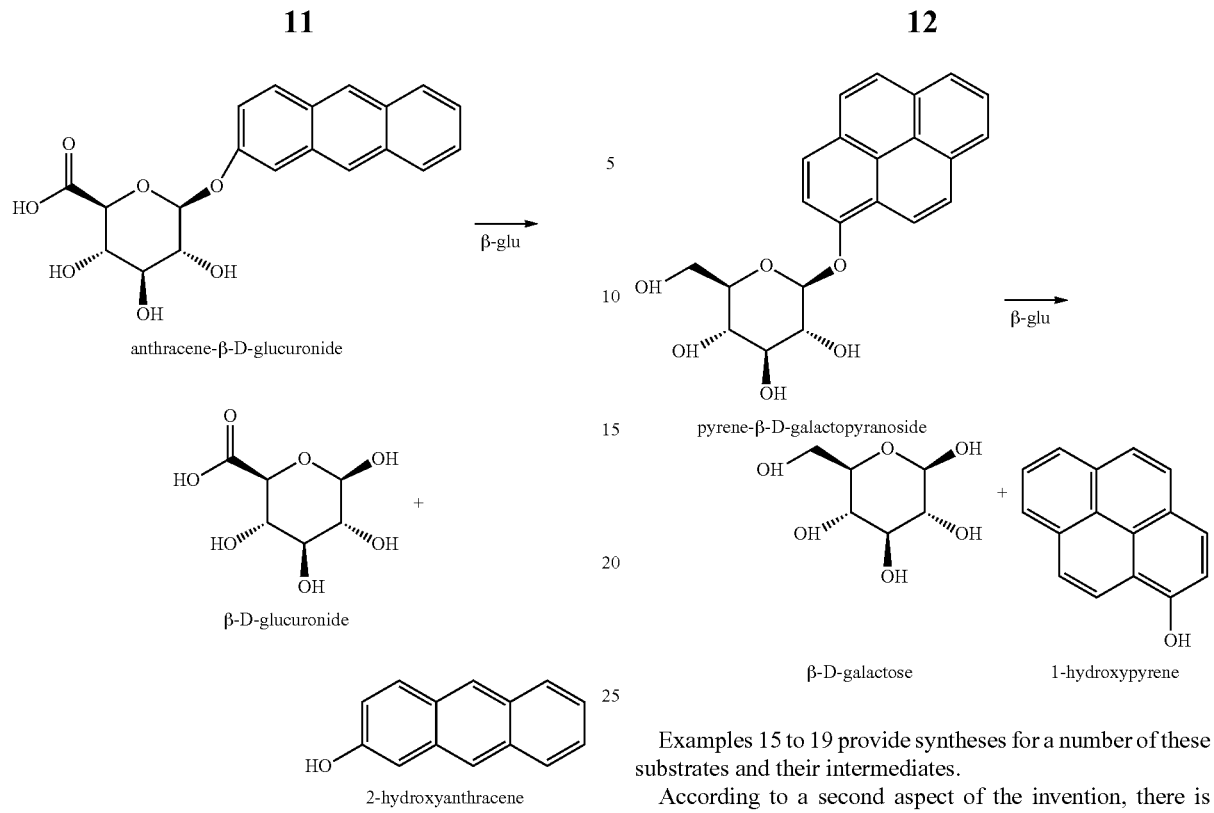

anthracene-β-D-glucuronide

β-D-glucuronide 2-hydroxyanthracene

When β-glu activity is detected with pyrromethene-β-D-glucuronide, the detected product is hydroxypyrromethene, as shown in the reaction scheme below:

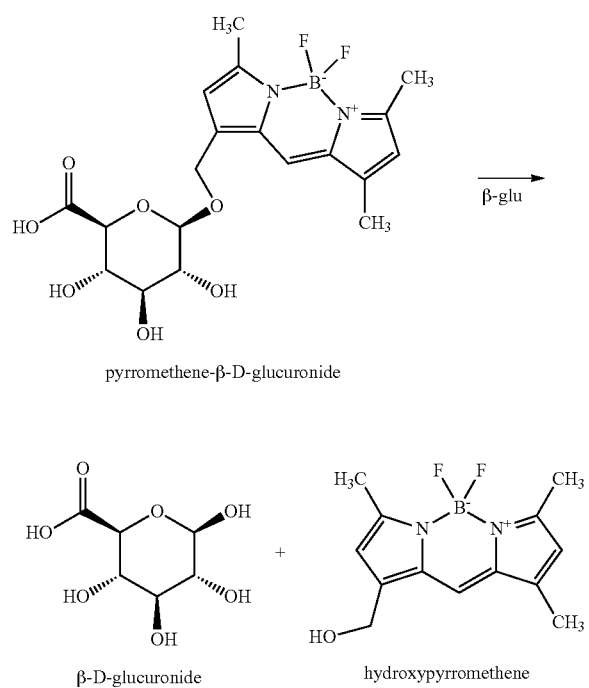

pyrromethene-β-D-glucuronide

β-D-glucuronide  hydroxypyrromethene

When β-gal activity is detected with pyrene-β-D-galacto-pyranoside (pyr-gal), the detected product is hydroxypyrene (HP), as shown in the reaction scheme below:

pyrene-β-D-galactopyranoside

β-D-galactose  1-hydroxypyrene

Examples 15 to 19 provide syntheses for a number of these substrates and their intermediates.

According to a second aspect of the invention, there is provided an optical probe for selectively-detecting fluorescent molecules. In particular, the optical probe provides for partitioning of molecules into the probe, wherein detected fluorescence is predominantly that of molecules partitioned into the probe. Such partitioning of molecules is achieved by disposing on the end of the optical probe a partitioning element. The partitioning element allows only a molecule of interest to be partitioned therein.

For example, to detect enzyme activity using a fluorogenic substrate and fluorescent enzyme-substrate product, the invention provides an optical probe having a partitioning element which allows for only the substrate or product molecules to partition therein, such that fluorescence of either the substrate or the product is detected. Thus, it matters not whether both the substrate and the product are fluorescent, as the optical probe detects fluorescence from only one of the two. Enzyme activity can then be determined by measuring the rate of disappearance of substrate fluorescence, or the rate of appearance of product fluorescence. In a preferred embodiment, product molecules are partitioned into the partitioning element, and enzyme activity is determined by measuring the rate of appearance of product fluorescence. As noted above, detection of enzyme activity according to the invention can be carried out in any medium where target enzymes are active. Generally, such media are aqueous, and they may be fluids (e.g., liquids) or semi-solids (e.g., biological tissues, gels).

According to one embodiment, shown schematically in FIG. 1, an optical probe 2 of the invention comprises an optical waveguide, such as an optical fiber, having a partitioning element 3 disposed at one end thereof. An excitation light source 4 and spectrometer 6 or other suitable device for detecting light are coupled via a coupler 7 to the opposite end of the optical fiber, such that light travels from the light source 4 to the partitioning element 3, and light received by the partitioning element 3 travels to an optical detector 6 (e.g., a spectrometer or CCD device). The wavelength of the light source 4 is chosen as appropriate for excitation of the fluorescent target molecules of interest, and is usually in the ultraviolet (UV) range for biological molecules. However, the invention is applicable to other wavelengths and target molecules. Examples of suitable excitation light sources are light-emitting diodes (LEDs), laser diodes, and lasers. In an alternative embodiment, the excitation light source 4 is discrete from the probe, such that the coupler 7 is not needed. The selection of excitation wavelength specific to the target molecule and/or the monitoring of emission wavelength specific to the target molecule improves the specificity and sensitivity of detection.

In the example of FIG. 1, the probe 2 is immersed in a sample solution 8 comprising substrate molecules 10 and target enzyme 12, or cells (e.g., microorganisms) bearing target enzyme 12. When cells are used, a membrane 18 is optionally provided for cell adhesion. Substrate molecules 10 are converted by target enzyme 12 to product molecules 14 and fluorescent product molecules (i.e., target molecules) 16. The partitioning element 3 provides for the partitioning thereinto of either the substrate molecules or the fluorescent product molecules; preferably the latter. Thus, product molecules 16 partition into the partitioning element 3, whereupon they are irradiated with excitation light from the light source 4. Fluorescence emitted from the target molecules 16 is detected by the spectrometer 6 or other suitable device.

Figure 2A:
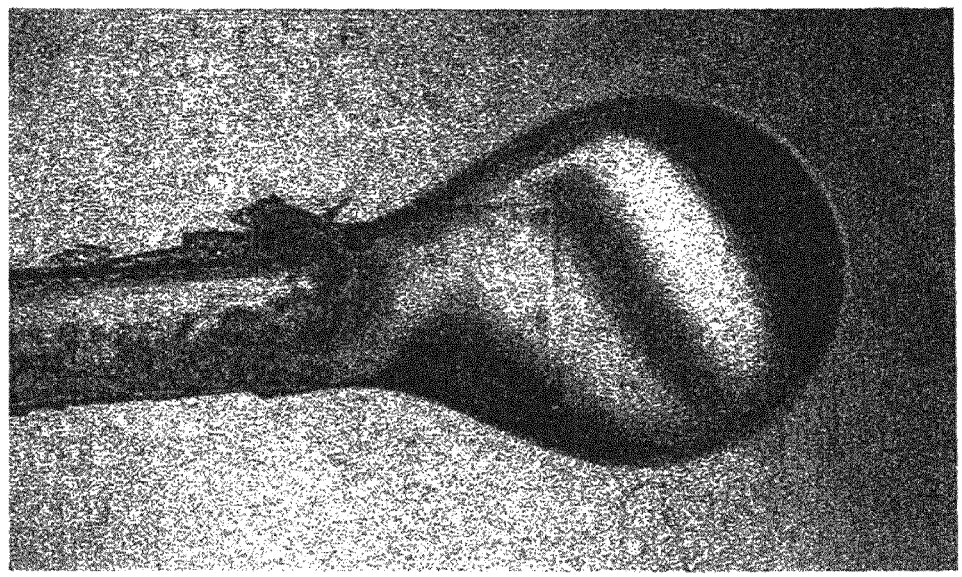
FIG. 2A is a photomicrograph of an embodiment of an optical probe according to the invention.

According to one embodiment, the partitioning element of the optical probe comprises a polymer film disposed on one end of the optical fiber, so as to cover the optical aperture of that end of the fiber. FIG. 2A is a photomicrograph of such a fiber-optic probe made with a 600 µm diameter optical fiber (see Example 1). Properties of the polymer material, such as molecular weight and degree of cross-linking, which determine the polymer's physical properties (e.g., viscosity and hardness (shore A)) are chosen so as to selectively provide for partitioning of a fluorescent molecule of interest.

Figure 2B:
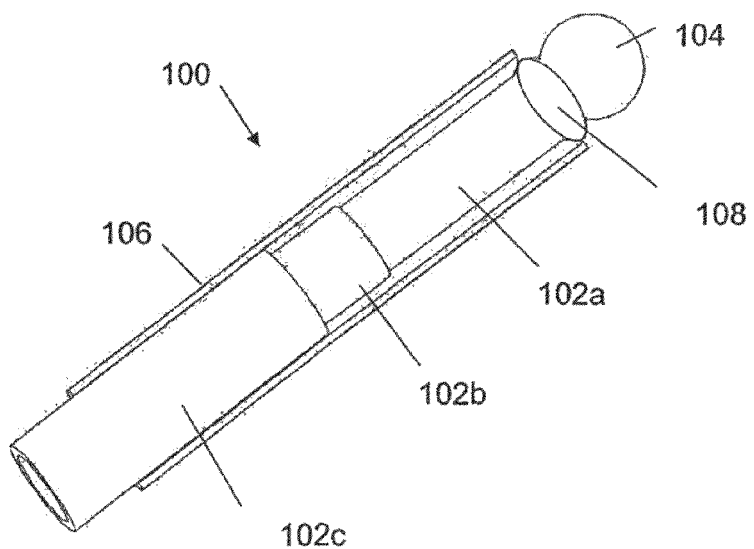
FIG. 2B is a schematic diagram of another embodiment of an optical probe according to the invention.

In a preferred embodiment, shown schematically in FIG. 2B, the optical probe 100 comprises a spherical partitioning element 104 attached to one end of an optical fiber. The optical fiber has a core 102a, a coating 102b, and a jacket 102c. The optical fiber is terminated at its other end by a suitable connector, such as an SMA connector (not shown), for ease of connection to associated equipment. The spherical partitioning element can be prepared in a range of sizes and with various rigidity using different polymer formulations. In general, spherical partitioning elements of about 0.2 mg to about 3.0 mg can be used. Preferably, the diameter of the spherical partitioning element substantially matches the diameter of the optical fiber used. The inventors have found that a 600 micron optical fiber produces good performance, when outfitted with a spherical partitioning element of substantially equal diameter. Performance can be further improved by attaching a half-sphere (i.e., hemisphere) partitioning element to the optical fiber, as this reduces the volume of the partitioning element without compromising sphere diameter.

As shown in FIG. 2B, a rigid tube 106 of, for example, stainless steel, is used to protect the fiber core 102a and sphere-fiber joint 108. Stainless steel is a preferred material for the rigid tube 106, owing to its strength and corrosion resistance. The sphere-fiber joint 108 is made with a polymer material having substantially the same properties, such as refractive index, as the partitioning element 104, and is used to affix the sphere 104 to the optical fiber and rigid tube. The polymer joint should plug the end of the rigid tube to prevent any liquid entering between the tube and the fiber coating and jacket. Methods for preparing such a fiber-optic probe are provided in Example 19, below.

In an embodiment suitable for detection of hydroxypyrene product molecules in an aqueous solution using, for example, the pyr-glu substrate discussed above, the partitioning element is comprised of a transparent, hydrophobic polydimethylsiloxane (PDMS) elastomer. Hydroxypyrene partitions into PDMS from aqueous solution, whereas the pyr-glu substrate does not partition into PDMS. Thus, hydroxypyrene fluorescence is detected by the optical probe. The rate of appearance of hydroxypyrene in the PDMS film is linearly related to the concentration of enzyme in the sample solution, so that monitoring of the signal from the optical probe versus time provides a measurement of enzyme activity.

Examples of three suitable PDMS materials having different molecular weights and different degrees of cross-linking are GE RTV118 (General Electric), Sylguard 186 (Dow), and Sylguard 184 (Dow). For polymers supplied with a precursor material and a curing agent, variables such as the ratio of precursor material to curing agent, curing conditions, and the like, can be varied so as to manipulate physical properties of the polymer. Other polymers, such as GE RTV118 are supplied already mixed, and polymerize when exposed to air.

Examples of other materials suitable for the partitioning element include, but are not limited to, sol gels, resins, gels, composites, sorbents, polymers other than PDMS, polyurethanes, polyacrylates, and molecularly imprinted films.

To optimize the limit of detection (i.e., detect target enzyme activity at minimum enzyme concentration in the sample, or detect target molecule fluorescence at minimum concentration in the sample), the volume of partitioning element in the optical aperture of the fiber should be maximized, while to minimize response time, the cross-section of the partitioning element material should be narrow. For example, where the partitioning element is a film (e.g., FIG. 2A), the cross section of the element should be about 400 µm to about 800 µm, preferably about 500 µm to about 700 µm, and the thickness should be less than about 800 µm, preferably less than about 600 µm. A partitioning element with satisfactory performance for detecting a given target (i.e., product or substrate) molecule will represent a compromise between these features. Performance can be further enhanced by shaping the polymer film partitioning element into a cone, sphere, or hemisphere-shape. This enhances the selectivity of the probe by preventing detection of target molecules not partitioned into the polymer film, which limits background signal from a sample.

Strategies to minimize detection time include, for example, reducing the incubation time of the cells by optimizing growing conditions (e.g., temperature, nutrient medium), and reducing the number of cells required for generation of a signal by the partitioning element/optical probe. The latter can be achieved by optimizing one or more of the compatibility of the excitation light source and the detector for the product, the rate of substrate conversion to product by cells, and the partitioning element for the product. It is expected that such optimization of the invention will result in an improvement (reduction) of 3 to 4 fold in the detection time for a single cell, to 2 to 4 h.

While the description has been described in detail with respect to fluorescent target molecules, it will be appreciated that the invention can be applied to detection of enzyme activity and presence of microorganisms by detecting light other than fluorescence, such as, for example, bioluminescence or chemiluminescence, provided that the bioluminescence or chemiluminescence target molecules (substrates or products) can be partitioned into the partitioning element of the optical probe.

According to another aspect of the invention there is provided an automated system for detecting enzyme activity. For example, an automated system according to the invention can be used to detect glucuronidase and/or galactosidase activity in water, food, or soil samples, to detect *E. coli* and total coliform, when the appropriate substrates are used, as described in detail above. An embodiment of an automated system is shown schematically in FIGS. 3A and B. The system comprises at least one optical probe 3 made from an optical fiber 2 as described above, with a partitioning element, and associated optical components such as a suitable light source 4, a spectrometer 6 or other device for detecting light (e.g., charge-coupled device), an optical fiber bundle 7, connector 8, coupler 5, and the like, a vessel (sample incubator) 26 with a sample inlet and a waste outlet, suitable hardware (e.g., pumps, valves, and the like; not shown), and a control unit/computer interface 22 connected to the optical probe and to the sample incubator for controlling, for example, the addition of substrate(s) to the sample incubator and sample flow. The automated system can be further equipped with one or more additional probes 28 for monitoring variables such as temperature, chlorine concentration, pH, and turbidity of the sample, as these variables can affect the duration and signal threshold of the *E. coli* and total coliform tests. The computer interface 22 controls operation of the system and collects and reports data relating to the presence/absence of enzymes, and hence microorganisms, of interest. In some applications of the automated system, such as when used to monitor for the presence of *E. coli* and/or total coliform in water, the computer interface can be configured to shut off the flow of water in the event that such microorganisms are detected.

Figure 3A:
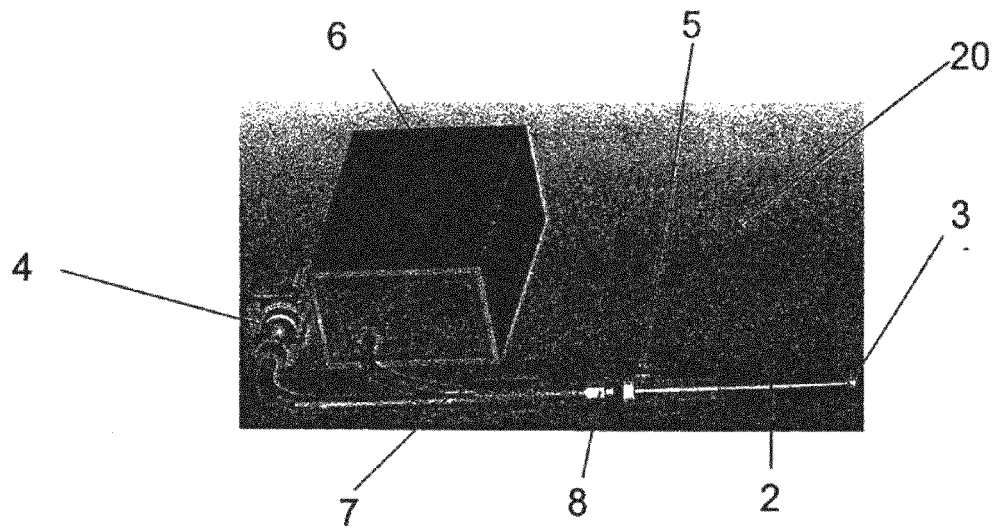
FIG. 3A shows an optical probe and associated optical components according to an embodiment of the invention.

As can be seen in FIG. 3A, the system comprises an optics package which delivers excitation light from a light source to the optical probe/partitioning element, and delivers fluorescence from the optical probe to a light-detecting device such as a spectrometer or a charge-coupled device (CCD). In one embodiment the optics package is a bifurcated fiber bundle; that is, a first optical fiber coupled at one end to ends of second and third optical fibers; the second fiber associated with the light source and the third fiber associated with the light-detecting device. A matching refractive index fluid is optionally provided to the region of the coupling of the three fibers to reduce scattered light. Preferably, all components shown in FIG. 3A, except the optical probe, are housed within a common chassis or enclosure.

In a preferred embodiment the first optical fiber is a 600 micron fiber (e.g., AS600/660UVPI, available from FiberTech Optika, Kitchener, Ontario, Canada), a low OH fiber with a polyimide coating and nylon jacket. This fiber is terminated at one end with a suitable connector, such as an SMA adapter, for connection to the optical probe. The other end of the first fiber is coupled to the second and third fibers. The second and third fibers may be of the same diameter as the first fiber, although use of smaller diameter fibers (e.g., 300 or 400 micron core) for the second and third fibers produces better coupling. In particular, use of 400 micron core (FiberTech Optika AS400/440UVPI), a low OH fiber with polyimide coating and nylon jacket, for the second and third fibers provides very good performance when coupled to the 600 micron first fiber. Coupling of excitation light, such as UV light, into the free end of the second fiber is enhanced by disposing a lens between the end of the fiber and the light source. In one embodiment, the lens is a spherical lens, such as a sapphire ball lens available from Melles Griot, Ottawa, Ontario, Canada. The free end of the third fiber is coupled to the light-detecting device. In embodiments where the light-detecting device is a CCD, the free end of the third fiber is aligned with one or more pixels on the CCD through a long-pass optical filter that prevents light at the wavelength of the light source from reaching the CCD.

Figure 3B:
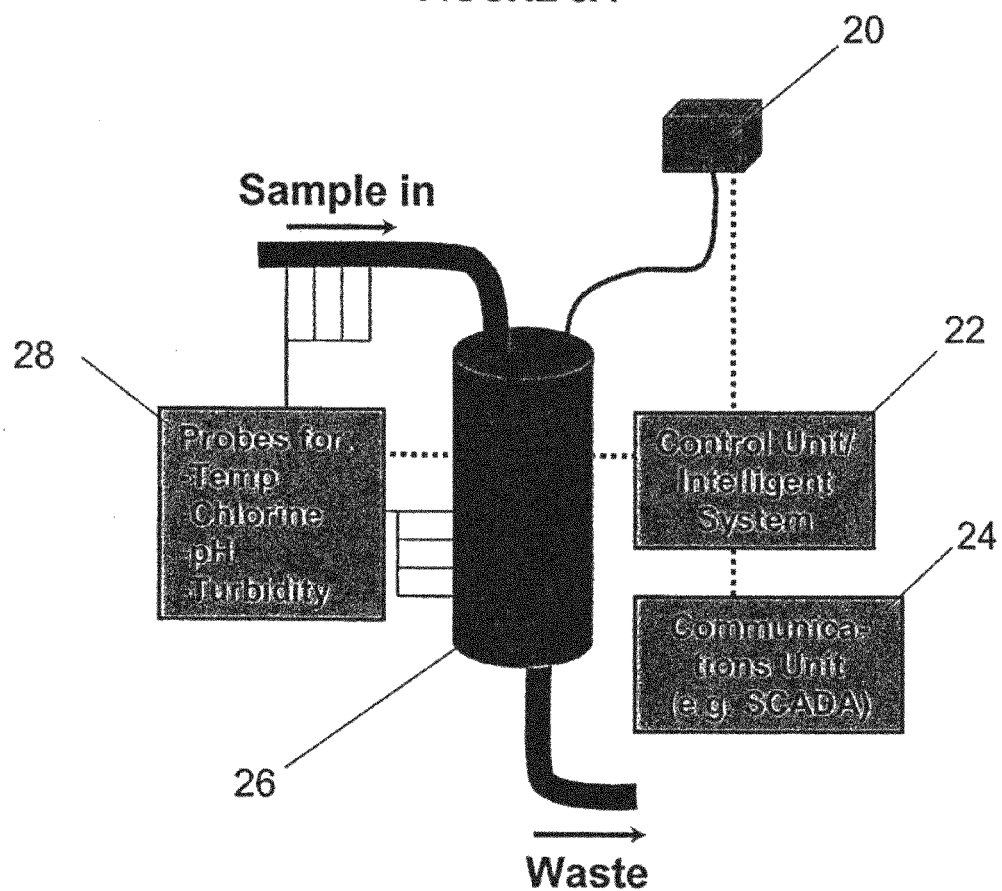
FIG. 3B is a schematic of an automated system for monitoring enzyme activity in accordance with the invention.

An automated system for monitoring water for the presence of microorganisms can be installed in single-family dwellings, schools, hospitals, municipal buildings, etc., and, in particular, in such dwellings and institutions with wells, and in municipal/city water distribution networks. In the latter, it is expected that automated systems would be installed at the water source (e.g., water treatment plant), at pumping stations, and at various nodes within the distribution network, and each automated system connected to a communications network using suitable communications hardware/software 24 (see FIG. 3B). Such automated system would provide, for example, real-time information to operators as contamination approaches unacceptable levels, such as warnings, with tolerance ranges, at various urgency levels, and where within the distribution network contamination is detected. The system could also automatically shut off distribution of contaminated water at an affected node(s). For ease of installation in new or existing water distribution systems, the automated system is preferably provided in a compact configuration using compact devices (e.g., a light-emitting diode (LED) light source CCD spectrometer).

In one embodiment the system is an automated sampler unit that employs a test cartridge with an integrated partitioning element that is capable of delivering presence/absence and bacteriological count estimation for a wide variety of pathogens, including, but not limited to, *E. coli* and total coliform bacteria. Preferably, the test cartridge is a disposable, single use cartridge. The system is based on the principles described above, but uses a cartridge with integral partitioning element in which individual samples are contained, rather than an optical probe. The partitioning element does not contact multiple samples, as might be done with an optical probe, thereby eliminating a potential source of cross-contamination between samples. The design also eliminates any need to clean an optical probe between tests. In a preferred embodiment, the system includes a calibration method based on multiple fluorophores that provides continuous optical path integrity monitoring and self-calibration. The system optionally provides for performing multiple tests for different pathogens.

Figure 3C:
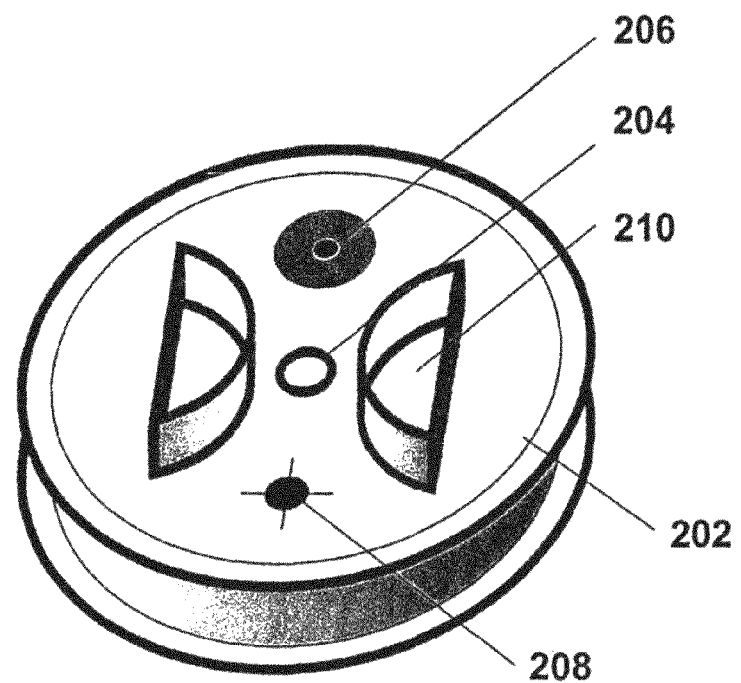
FIG. 3C is a schematic diagram of a test cartridge for use in an automatic sampler unit of the invention.

The test cartridge incorporates elements necessary to conduct a bacteriological test for a specific target pathogen, including but not limited to *E. coli* and total coliform bacteria. As shown in FIG. 3C, the test cartridge 200 comprises a sealed casing 202 enclosing a sterile interior, that can be easily manipulated by simple mechanics in an automated system. The partitioning element 204, and a test medium in either powdered or liquid form, are contained within the housing 202.

The test medium comprises one or more glucuronide or galactoside substrate materials, each substrate material comprising a target fluorophore, as described above. The test medium also comprises a second fluorophore (i.e., a calibration fluorophore) that dissolves in an aqueous environment to provide a baseline optical signal for calibration and monitoring of optical signal path integrity, and a growth medium to support growth of the target organism(s). The test medium may optionally comprise: sodium thiosulfate to remove free chlorine from a water sample; antibiotic to inhibit growth of non-target microorganisms; and a compound that reacts in the presence of the target pathogen to produce a colour change as visual confirmation of the presence of the target pathogen in the sample.

As shown in FIG. 3C, a hole or port 206 in the casing 202 is covered by a membrane or septum that allows for introduction into the cartridge of a sample in a manner that preserves the sterile field within the casing; e.g., by injection of a sample through the septum using a needle. Also disposed on the casing 202 is an alignment or indexing mark 208, that can be sensed automatically (e.g., optoelectronically), to facilitate manipulation and orientation of the cartridge by the automated system (e.g., facilitate correct alignment of the port 106 for injection of a sample), and for identification of the cartridge (e.g., identify the type of test medium contained therein), allowing the sampling unit to adapt to various types of tests for a variety of target pathogens. The cartridge is optionally further provided with fins, channels, or bosses 210 on one or more inner surfaces thereof, to facilitate mixing of the sample when the cartridge is rotated or agitated.

Figure 3D:
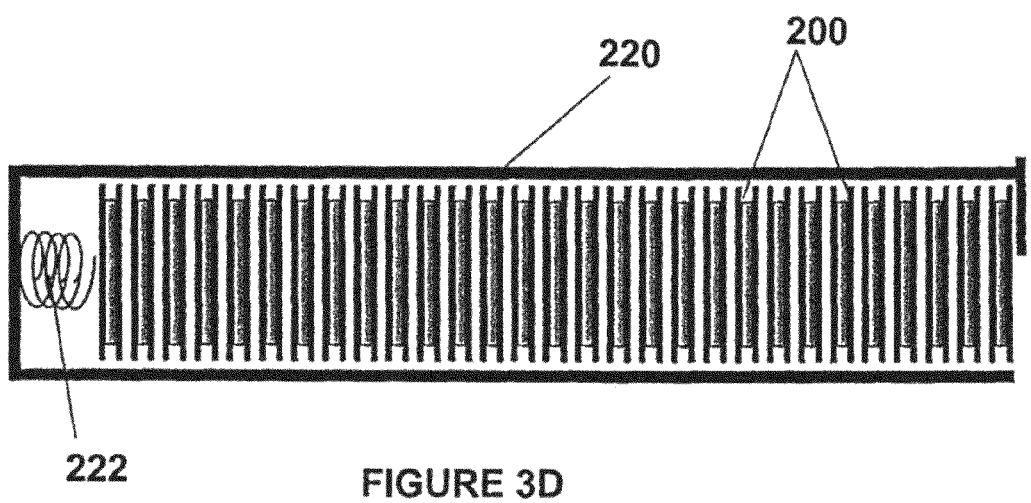
FIG. 3D is a schematic diagram of a magazine for holding one or more of the test cartridges shown in FIG. 3C.
Figure 3E:
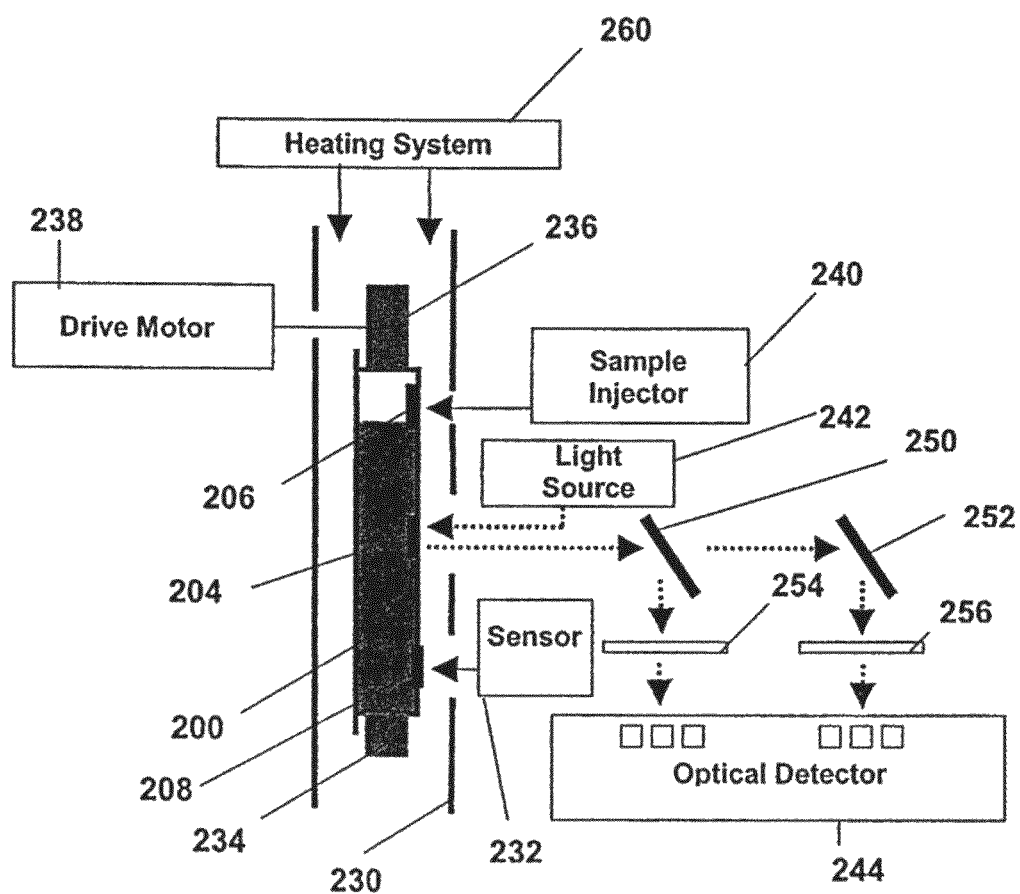
FIG. 3E is a schematic diagram of an automatic sampler unit according to the invention, wherein dotted lines represent the optical path.

In FIG. 3D there is shown a magazine 220 for holding a plurality of test cartridges 200, with a spring 222 or the like for keeping cartridges biased toward an end thereof. FIG. 3E shows schematically an embodiment of an automated sampler apparatus of the invention. The apparatus comprises a holder 230 for holding one or more test cartridges 200 in a test chamber. The test cartridge may be loaded into the holder manually or automatically from a magazine such as that shown in FIG. 3D. Test cartridges loaded into the magazine may be for only one type of target pathogen, or there may be a mix of test cartridges for various target organisms. For example, test cartridges may be for *E. coli* only, or a combination of *E. coli* and total coliform bacteria, and possibly other target pathogens as well. The indicator 208 on the test cartridge, together with an optoelectronic test/alignment sensor 232, allows the apparatus to distinguish between different cartridges. The holder 230 has support rollers 234, 236 for holding, rotating, and/or agitating a cartridge 200, via a motor and drive system 238. The apparatus may also include a sample injector 240 that injects a water or other sample into a cartridge though the cartridge intake port 206. Alternatively, cartridges may be injected with samples prior to being loaded into the apparatus. The apparatus may also include a heating system 260 for sample incubation, in which, for example, heated air is flowed through the holder 230.

The apparatus includes optics for detecting the fluorophore of interest (e.g., a fluorophore produced upon degradation of the substrate by target enzyme action). The optics together with the partitioning element function on the same principle as described above, and the optical path is represented by dotted lines in FIG. 3E. Thus, the apparatus includes a light source 242, such as a UV light source, for irradiating the partitioning element 204 of the cartridge 200, and an optical detector 244, such as a CCD, for detecting fluorescence of the target fluorophore partitioned into the partitioning element. The apparatus may also include optics for irradiating and detecting the calibration fluorophore, mentioned above, to provide a baseline optical signal for calibration and/or monitoring of the optical signal path integrity. In such embodiment fluorescence produced by the target and calibration fluorophores must be differentiated and detected. Thus, for example, the optical path for detecting fluorescence emitted from the partitioning element a beam splitter 250 and mirror 252 that splits the optical pathway into two channels. Each channel is filtered using an optical filter 254,256 at the wavelength of the fluorophore of interest (i.e., the target and calibration fluorophores), and the filtered optical signals detected.

The apparatus optionally includes a control panel to allow operators to control its operation, a data acquisition/processing/display device, and a remote control interface (via, for example, the internet or telemetry) to allow the apparatus to be interfaced with supervisory control and monitoring, data logging, and diagnostics systems, commonly referred to as SCADA systems.

The automated water sampler unit of the invention has several features which ensure reliability of the detection result. For example, as noted above, the test cartridge uses an additional fluorescent molecule (i.e., the calibration fluorophore). This can conveniently provide for calibration of the partitioning element of each test cartridge and optical components of the system. Another convenient function of the calibration fluorophore is to provide continuous integrity monitoring of the optical path throughout the test, as failure of the optical path could result in a failure to detect the luminescence of the detection fluorophore, resulting in a false negative result. Integrity of the optical path is ensured through use of a CCD-based detector, wherein irradiation across multiple pixels on the CCD array provides redundancy of detection.

The system may optionally be provided with one or more of the following:

1. Re-testing of a sample upon obtaining a positive (adverse) result.
2. Injection of chlorine into completed water test to reduce biohazard potential of an adverse water sample.
3. Introduction of a colour indicator in the substrate to provide visual confirmation of an adverse water sample.
4. Use of free-space optical sensing techniques to acquire the optical signal from the partitioning element embedded in the test cartridge, or use of a polished fiber-optic segment to provide friction-fit interface to the partitioning element.
5. Inclusion of multiple test chambers within the same apparatus, consisting of sample injectors, heating systems, and optical detectors for the partitioning element, that allow multiple tests to be conducted in parallel—either to provide time cascading of samples (e.g., every 2 or 4 hours) or to provide multiple target pathogen tests (e.g., *E. coli* and total coliform running simultaneously on the same apparatus).

The following is an example of major steps performed by an automated water sampler unit (AWSU) of the invention during a test cycle:

1. A test cycle is activated using the control panel or by a remote activation command through the SCADA interface.
2. The test chamber is pre-heated to the required temperature (e.g., 35 to 42° C.).
3. A test cartridge is selected from the cartridge magazine and is loaded into the test chamber.
4. The test cartridge is engaged by a roller mechanism that rotates the cartridge to align the cartridge and to provide agitation throughout the test cycle.
5. The test cartridge is aligned using the alignment/test ID indicator to align the septum with the needle injector.
6. A water sample of the required volume (e.g., 100 mL) is injected (after a runout of residual water in the sample line) into the test cartridge. An inline flow meter is used to measure the required sample volume.
7. The needle injector is cleaned and sterilized using a chlorine or alcohol solution.
8. An internal timer is activated and a SCADA signal is sent with the test type ID and sample initiation time.
9. The test cartridge is rotated continuously to ensure that the substrate is dissolved and mixed with the test water sample.
10. The water sample dissolves the substrate mixture, including the water-soluble calibration fluorophore.

11. The optical path is activated and is monitored for baseline indications of the calibration fluorophore.
12. Sample rotation and agitation is maintained for a test period of up to 20 hours.
13. Throughout the test period, the optical path is monitored for indication of both the calibration fluorophore (to provide continuous optical integrity path monitoring) and the target fluorophore (indicating the presence of the target pathogen in the water sample).
14. Optical pathway status, pathogen detection status, and diagnostic status data are periodically sent through the SCADA data channel for logging and reporting.
15. Alarms for the presence of, and estimated count of, the target pathogen are provided aurally and visually on the front panel of the unit and are sent through the SCADA data channel for logging, reporting, and operator action.
16. At the end of the test period, the sample test cartridge is ejected into a waste container and the system is re-set to conduct another test.

In accordance with yet another aspect of the invention there is provided a kit for detecting enzyme activity. The kit comprises an optical probe, associated optical components and optionally other components such as an incubator, as described above, and preferably is compact and low-cost, so as to be useable and affordable by individuals such as homeowners who wish to test and monitor water or other samples for the presence of contaminating microorganisms such as *E. coli* and total coliform In yet a further aspect of the invention, measurement of enzyme activity is coupled with enzyme-linked immunoassay (EIA), permitting detection of a wide variety of target species including, without limitation, chemical and microbiological contaminants in samples, e.g., in water. Enzyme-linked immunosorbent assay (ELISA) is a preferred embodiment. Specificity and selectivity in recognition of the target species are conferred by the antibody employed in the immunoassay. Quantification of the target species is provided by the detection of a fluorescent species (label) produced by the enzyme. The label is detected as described above by employing a partitioning element.

The assay of the invention can use any enzyme used in any standard immunoassay, such as, for example, alkaline phosphatase (AP). To monitor AP or other enzyme activity, a substrate with a phosphate moiety attached to a fluorescent compound is used, where the product fluorescent compound is one which will be partitioned into the partitioning element of the optical probe.

Classes of contaminants that may be detected by immunoassay include, but are not limited to, hormones, estrogenic compounds, pesticides, biological toxins, polynuclear aromatic compounds, and polychlorinated biphenyls.

In some embodiments of this aspect of the invention, EIA includes a "competitive binding" assay. In a first embodiment, an enzyme is conjugated to a compound such that the conjugate can compete with the target compound for binding to an antibody. This results in an amount of conjugate complexed with antibody that is inversely proportional to the amount of target compound present. A calibration or "competitive binding" plot is developed by first isolating the antibody complex from the unbound conjugate, and then measuring the enzyme activity for a series of standard target contaminant concentrations. See Example 20 set forth below.

In a second embodiment employing competitive binding, a secondary label (often a protein, such as, e.g., bovine serum albumin, or a chemical species) is conjugated to a compound such that the secondary label/compound conjugate can compete with the target compound for binding to an antibody. After the competitive binding step, a secondary antibody that binds the secondary label is added, the secondary antibody being linked to an enzyme. As above, the antibody complex is separated from unbound conjugate, and the amount of complexed label is inversely proportional to the amount of target compound in the original sample.

In other embodiments of the invention, EIA involves a "sandwich" assay (e.g., ELISA) for detection of a target compound. Such embodiments are generally preferred for detection of biological contaminants. In an example of a sandwich assay, an antibody which is specific for a target of interest is immobilized on a solid support. A sample is introduced on the support surface. Contaminants having the target (which may be cells) bind to the antibody and become immobilized. To determine the number of immobilized contaminants, a second antibody is added which also recognizes the contaminants and binds to them. This second antibody can either be unlabelled or it can be previously linked to an enzyme. If the second antibody is unlabelled, then a third antibody which is linked to an enzyme is added, the third antibody recognizing and binding to the second antibody. In either case, the result of this procedure is an amount of immobilized enzyme which is directly proportional to the number of target contaminants present in the original sample. The chosen enzyme produces a product, conveniently a fluorescent product, which is detected as described herein. A calibration plot is developed by measuring the enzyme activity for a series of standard solutions containing known contaminant (e.g., cell) levels.

According to this aspect of the invention, EIA can be used for detection of biological contaminants (including, but not limited to, *E. coli*, total coliform, *Giardia lamblia, Chryptosporidium arvuum*, and *Pseudmonas aeriginosa*) in samples such as water, food, biological samples, and soil. Advantageously, it can be used for detection of biological contaminants which cannot otherwise be detected by measurement of biological activity of the contaminant itself. Classes of biological contaminants for which immunoassays can conveniently be used include, but are not limited to, bacteria, protozoa and viruses. Specific examples in each class include, but are not limited to, for bacteria, *Escherichia coli* 0157:H7, *Pseudomonas aeruginosa*; for protozoa, *Cryptosporidium parvuum* and *Giardia lamblia*; and for viruses, Norwalk and SARS viruses. In particular, the assay is useful for detecting *Giardia lamblia, Chryptosporidium arvuum*, and *Pseudmonas aeriginosa* in samples, as these organisms do not have glucuronidase or galactosidase, and hence would be suitable for the detection schemes based on these enzymes described above.

The invention has distinct advantages over current methods for measuring enzyme activity. For example, the most commonly used methods employ substrate/product combinations in which optical properties (absorbance of light or emission of fluorescence) change on conversion of the substrate to the product. Several substrates are available where significant optical changes do occur on enzyme conversion, but the requirement for this change places significant restrictions on the substrates which can be used. Enzymes such as β-glu catalyze cleavage of chemical bonds, usually by hydrolysis, which means removing an oxygen-linked substituent from the substrate and replacing it with a hydroxy group (i.e., conversion from an ether to a hydroxylated form). Conventional substrates are therefore limited to compounds which undergo a significant optical change on conversion from an ether form to a hydroxyl form. Some compounds, such as hydroxycoumarin compounds, do undergo such changes. Many other compounds which can be detected with greater sensitivity, including polycyclic aromatic hydrocarbons (PAHs), do not change optical properties significantly with such a conversion.

In contrast, in the invention the product is distinguished from the substrate based on differential partitioning into the partitioning element of the optical probe. This means that a change in the chemical properties of the compound is required, i.e., from a form which does not partition into the partitioning element to a form that does, whereas a change in optical properties is not required. As a result, a wide range of compounds not available to conventional methods can be used as substrates in accordance with the invention. For example, PAHs, which emit fluorescence both before and after conversion to product, are suitable substrates. In the above embodiment relating to detection of β-glu activity, pyr-glu is a glucuronide-form of a PAH which is substantially water-soluble and will not partition into a hydrophobic film like PDMS. The product HP is much less polar and partitions readily into PDMS.

The invention offers further advantages. The entire optical path for fluorescence excitation and emission is contained inside the optical probe, and in particular, in the partitioning element, such that light does not have to penetrate the solution in the measurement. This means that enzyme activity may be detected in opaque or highly scattering media directly. The probe/partitioning element provides a continuously monitored signal, which simplifies analysis of kinetics as required in enzyme activity measurements. Finally, the sensitivity of the probe/partitioning element is in part determined by the partition constant ($K_{fs}$) for the product, defined as the ratio of the compound concentration in the partitioning element to the concentration in solution. In cases where $K_{fs}$ is greater than one, the product is 'preconcentrated' into the partitioning element. The greater the value for $K_{fs}$, the higher the sensitivity for detection. Values of 10,000 or greater are typical for PAHs.

The contents of all cited publications are incorporated herein by reference in their entirety.

The invention is further described by way of the following non-limiting examples.

WORKING EXAMPLES

Example 1

Optical Probe

An optical probe was fabricated from a 1 m length of a single 600 μm diameter Nylon®-clad silica fiber (Fiberguide Industries, Stirling, N.J., U.S.A. or FiberTech Optika, Kitchener, Ontario, Canada). A first end of the fiber was prepared for optical interface with other instruments, and a partitioning element was affixed to the second end of the fiber. The first end of the fiber was prepared by removing 4 cm of the cladding, scoring the fiber with a ceramic blade, and twisting and pulling so as to break the fiber leaving a planar surface. For the partitioning element, a transparent, hydrophobic polydimethylsiloxane (PDMS) elastomer film was applied to the second end of the fiber. Probes were made from three PDMS materials having different molecular weight starting materials and different degrees of cross-linking.

GE RTV118 (General Electric) films were made by mixing 50 mg of the PDMS precursor material with 300 μl dichloromethane (DCM) and then allowing the DCM to evaporate until the mixture became tacky (3 h static or less time by blowing with nitrogen). An 18-gauge syringe tip was used to apply a bead of the tacky PDMS onto the exposed tip of the fiber and the bead allowed to cure for 24 h at room temperature.

Sylguard 186 (Dow) films were made by mixing the base material and curing agent in a 10:1 ratio by volume. This mixture was dissolved in a 3× volume of dichloromethane (DCM). This mixture was allowed to cure for 5 h at room temperature with evaporation of DCM. An 18-gauge syringe tip was used to apply a bead of mixed Sylguard 186 (viscosity=65,000 cp; shore A=24) onto the exposed tip of the fiber and the bead allowed to cure for 48 h at room temperature. An example of this type of bead is shown in FIG. 2. The bead was then trimmed using a scalpel to remove the elastomer that was not directly in the path of the excitation light. A conical end was also fabricated using a scalpel to reduce probe volume and background scatter.

Sylguard 184 (Dow) films were made by repeating the Sylguard 186 procedure, above, but produced much thinner films (viscosity=3900 cp; shore A=50). To obtain a thicker film, the prepared fiber was placed vertically in an oven at 90° C. for 30 minutes. The Sylguard 184 was prepared by mixing the base material and curing agent in a 10:1 ratio by volume. While the fiber was still warm, the tip was contacted with the mixed Sylguard 184. This caused the elastomer to cure rapidly on the fiber tip and was repeated several times until the film resembled a bead of appropriate dimensions (e.g., FIG. 2). The bead was then trimmed using a scalpel to remove elastomer not directly in the path of the excitation light (see below).

Example 2

Experimental Set-up and Characterization of the Optical Probe

Figure 4:
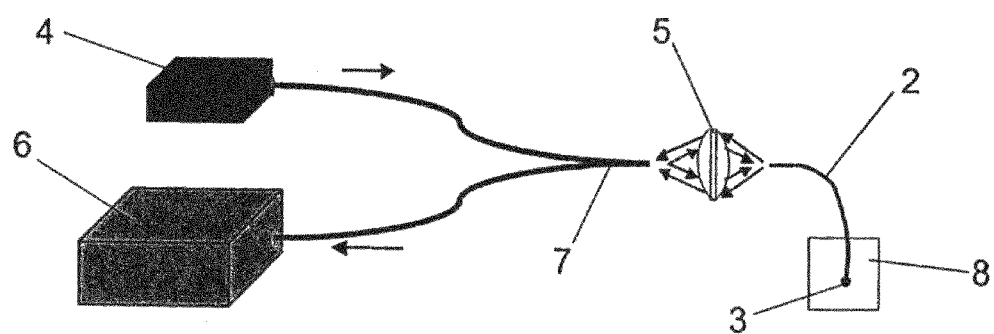
FIG. 4 is a schematic diagram of an optical probe and apparatus configured to detect enzyme activity.

The experimental set-up is shown in FIG. 4. This setup allowed for scanning of excitation and emission spectra, and also for monitoring emission at a fixed wavelength as a function of time, and for producing sensor time response curves. The optical probe 3, made from a length of optical fiber 2, was connected via an optical coupler 5 and optical fiber 7 to an excitation light source 4 and a spectrometer 6. The light source 4 included a computer-controlled scanning monochromator coupled to a xenon lamp (both from Sciencetech Inc., London, ON) to select excitation wavelength, and the spectrometer 7 included a similar monochromator with a photomultiplier detector to monitor the emission at a longer wavelength.

Figure 5:
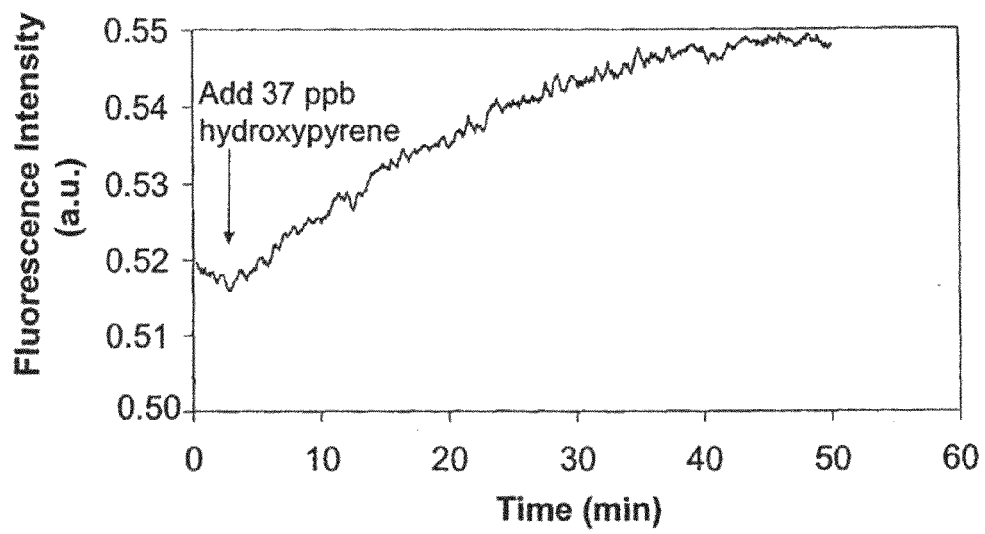
FIG. 5 is a plot showing rate of partitioning of hydroxypyrene into a PDMS optical probe according to one embodiment of the invention.
Figure 6:
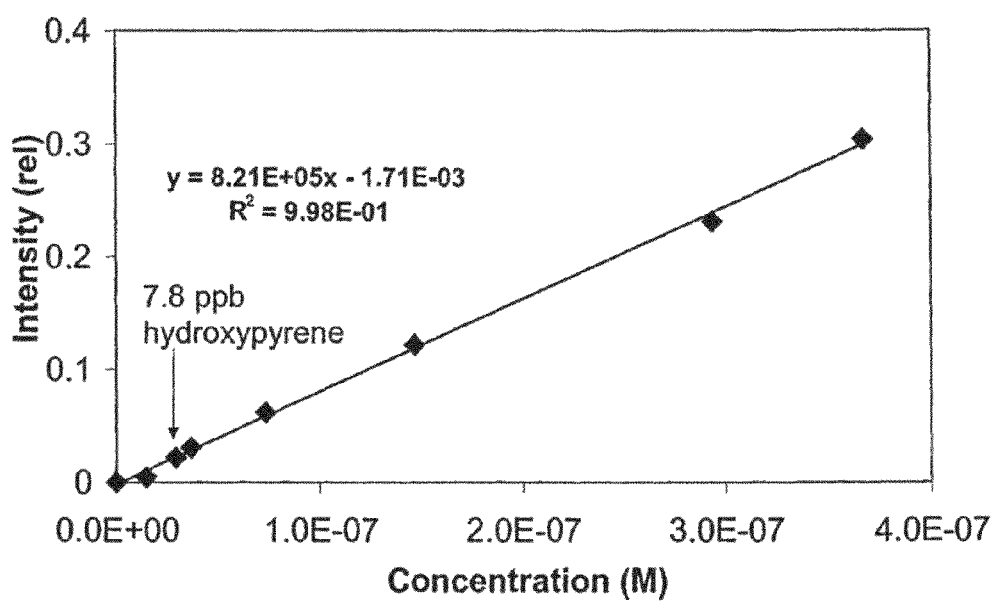
FIG. 6 is an optical probe calibration curve for hydroxypyrene.

Several optical probes were prepared using the procedure described above. Initial characterization of the optical probes was done by direct addition of product compound, 1-hydroxypyrene, to a solution containing a probe. Response time of a probe made with GE RTV118 is shown in FIG. 5. Equilibration occurred in 30 to 40 minutes for this probe, with the other probes giving similar response times (data not shown). After equilibrating, fluorescence detected by the probe was linearly related to concentration of HP, as shown in FIG. 6. A similar plot for the substrate pyrene-β-D-glucuronide gave a slope of zero, indicating no detection of the substrate.

Example 3

Detection of Enzyme Activity

Figure 7:
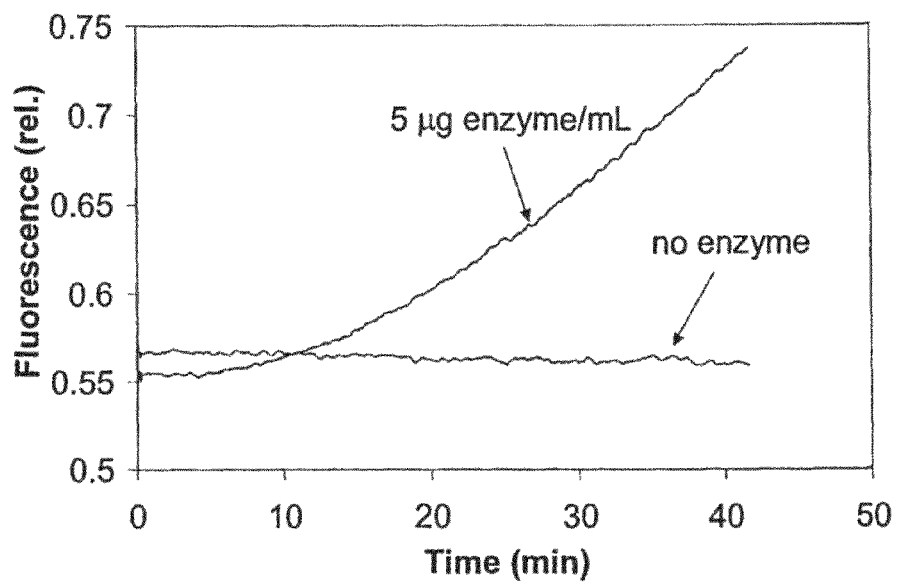
FIG. 7 is a plot comparing fluorescence detected by an optical probe of the invention in the presence and absence of an enzyme.
Figure 8:
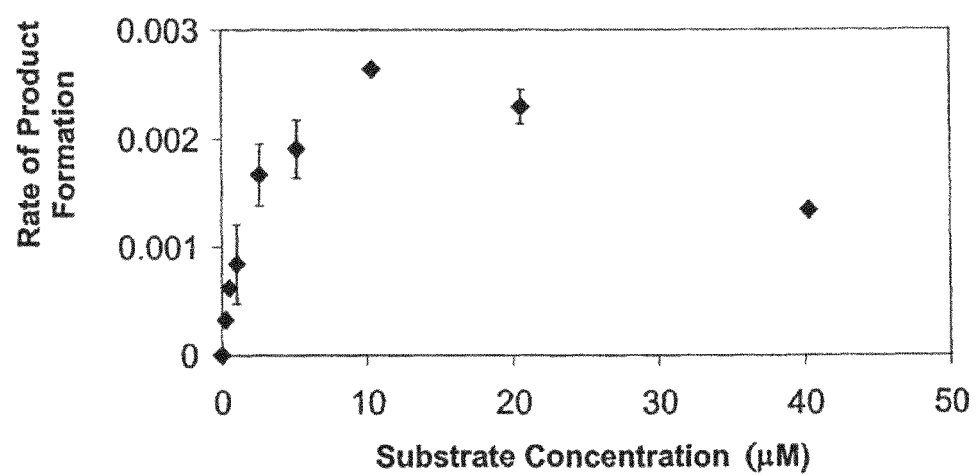
FIG. 8 is a plot of rate of target molecule formation as detected by an optical probe of the invention, as a function of substrate concentration, for the enzyme glucuronidase.
Figure 9:
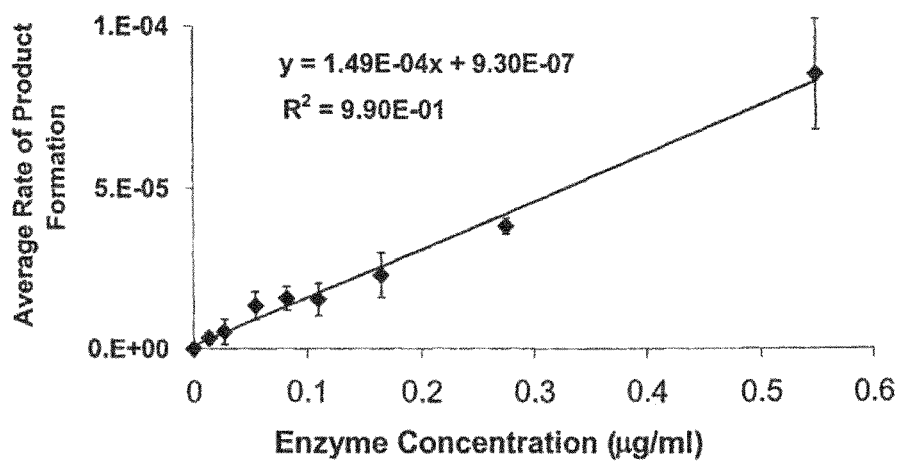
FIG. 9 is a calibration curve of glucuronidase activity based on fluorescence detected by an optical probe according to an embodiment of the invention.

Operation of the probe for detecting enzyme activity was demonstrated by inserting the probe into a substrate solution, allowing stabilization, and then adding the enzyme (E. coli-derived β-glu and β-gal were obtained from Sigma). After an initial delay, an increase in fluorescence was seen over 30 min (FIG. 7). The slope of the curve from 20 min to 30 min was used as a measure of relative enzyme activity. The optimum substrate concentration was determined to be 10 µM by plotting measured enzyme activity at various substrate levels (FIG. 8), and this concentration was used in subsequent experiments. A plot of measured enzyme activity vs. amount of enzyme added was linear (FIG. 9), indicating the ability to quantify enzyme activity with the probe, and to detect as little as 10 ng/ml enzyme levels.

Example 4

Optical Probe Detection of *E. coli*

Figure 10:
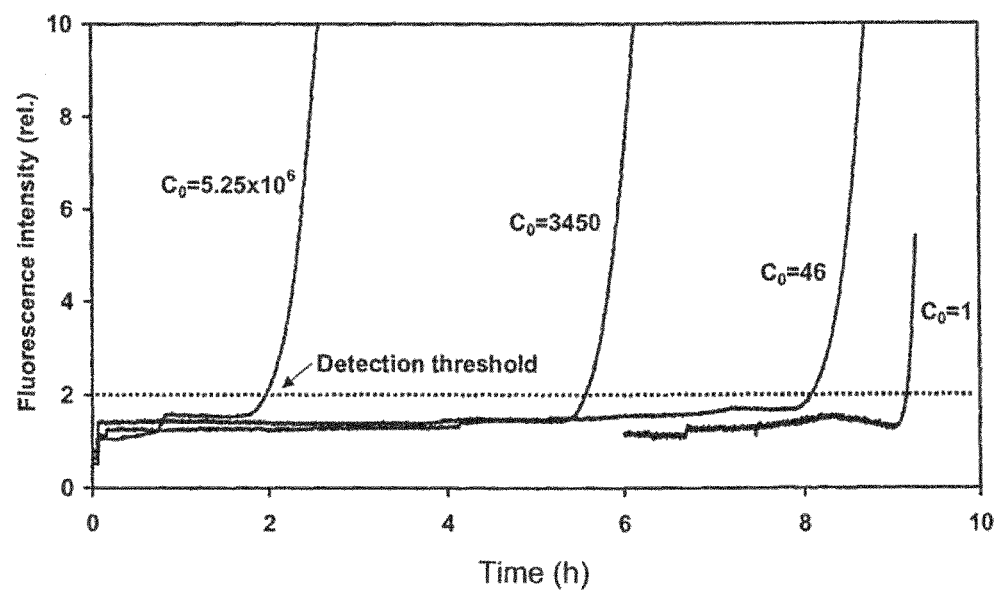
FIG. 10 is a plot showing optical probe detection of E. coli for various initial concentrations of E. coli cells.

*E. coli* B (stock No. 413) cell numbers were determined by a combination of optical density and plate count measurements. Samples containing various initial numbers of cells were placed in glass vials with standard Luria broth and 10 µM substrate added (total volume of each sample was 4 mL) and the incubation temperature was maintained at 37.0±0.1° C. Samples were tested one at a time by inserting the optical probe into the sample, and monitoring the fluorescence signal as a function of time. After 1 to 10 h, the signal increased rapidly if one or more *E. coli* cells were initially present in the sample (see, e.g., FIG. 10). Control experiments (cells killed by freeze-thaw cycle) gave no response after 24 h. The time between insertion of the probe into the sample and onset of the signal (defined as an increase of 1 V above background level) was inversely related to the number of cells originally added, in agreement with a model for kinetic analysis of cell growth (see FIG. 11 and the following example).

Example 5

Kinetics of *E. coli* Growth and Quantification of *E. coli*

We assume that the signal versus time data obtained (see FIG. 10) may be described using a simple kinetic model for cell growth, where the optical probe reports the product concentration, which is a function of the number of cells present. With this assumption, the optical probe gives a positive signal when a critical number of cells has been generated in the detection vessel. We define the initial number of cells in a sample as $C_0$, the number required for detection as $C_d$ (note: cell density as number/mL can be used in place of cell number), the time for the number of cells to double as $t_2$, and the time required for detection as $t_d$. The number of cells at any time ($C_t$) may be written:

$$C_t = C_0 \cdot 2^{\frac{t}{t_2}}$$

and at detection time:

$$C_d = C_0 \cdot 2^{\frac{t_d}{t_2}}$$

This can be transformed to:

$$\ln(C_d) = \ln(C_0) + \frac{t_d}{t_2}\ln(2)$$

Which is rearranged to:

$$\ln(C_0) = \ln(C_d) - \frac{\ln(2)}{t_2}t_d$$

Using the pyrene-β-D-glucuronide substrate, a series of experiments with known $C_0$ (determined separately through plate counts) was conducted, and the time to detection $t_d$ determined. A plot of $\ln(C_0)$ versus $t_d$ was linear (FIG. 11A), with the slope giving $-\ln(2)/t_2$ and the intercept giving $\ln(C_d)$.

From linear regression of the resulting plot, the doubling time $t_2$ was calculated to be 20.3 min, and the critical number of cells for detection $C_d$ was determined to be $3\times10^8$.

The linearity of the plot (FIG. 11A, $R^2 > 0.99$) supports this model for the overall behaviour, and lets us calculate the number of cells at points in time before detection. Using this, we can now take a particular curve, e.g., $C_0=1$ cell, and for any specified time, we can estimate the number of cells present. When detection occurs at a specified time for an unknown sample, the same plot can be used to determine the number of cells present initially, so quantification of *E. coli* in the sample is possible. This assumes the same doubling time for the sample and the reference experiments, which can be determined for a wider variety of samples.

Figure 11A:
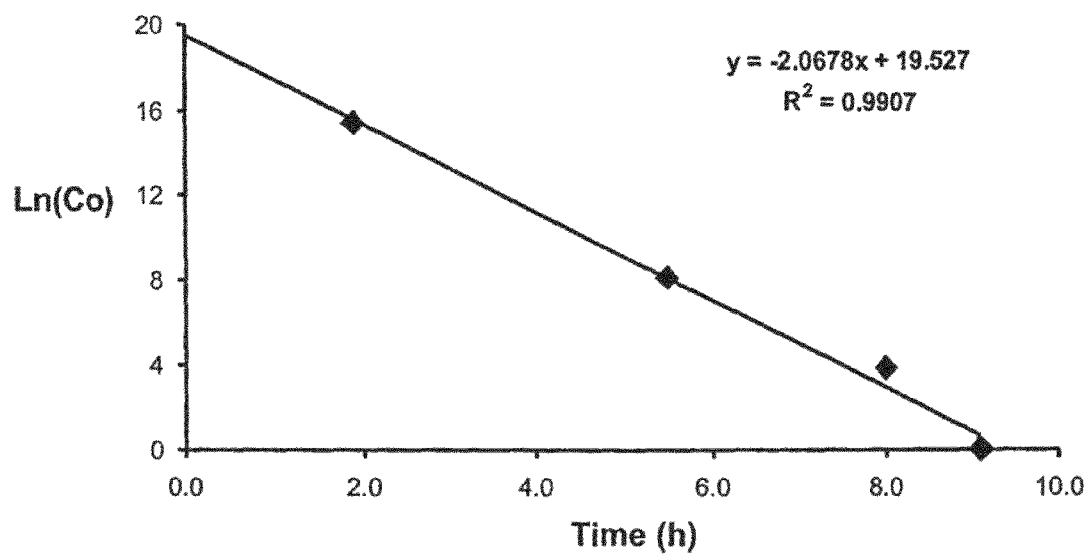
Figure 11B:
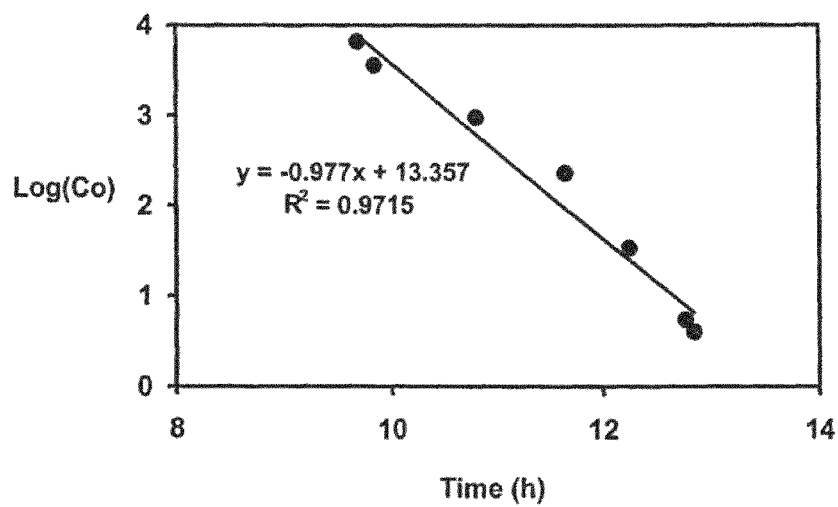
Figure 11C:
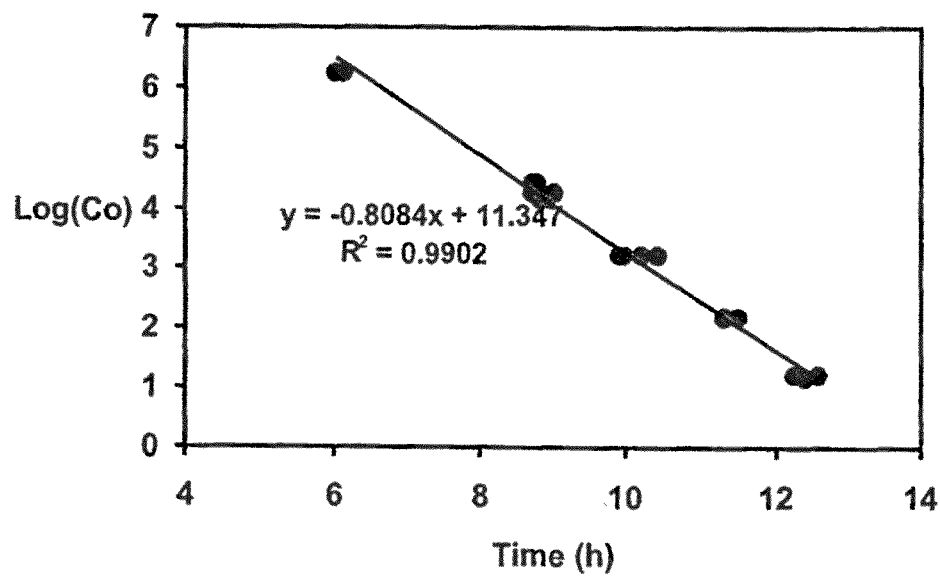
Figure 11D:
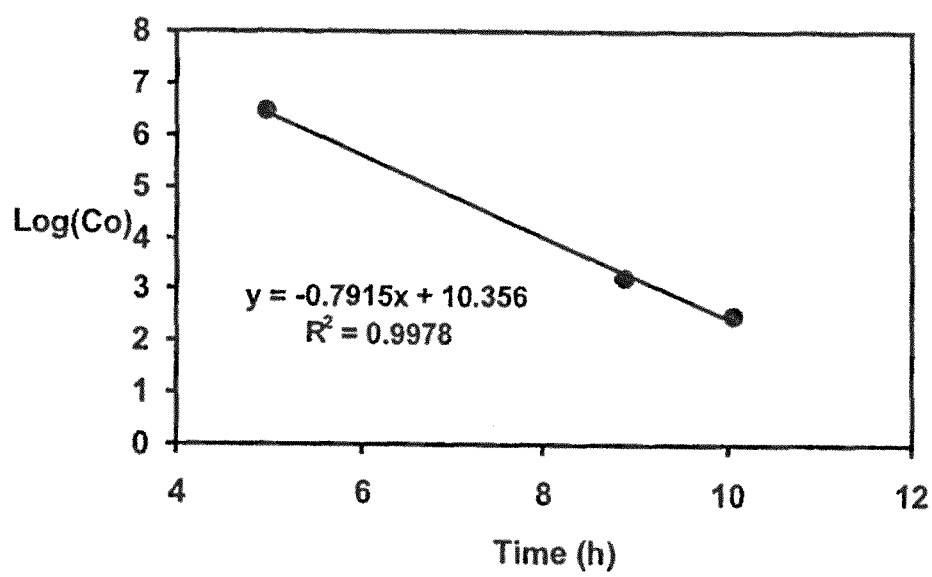

This experiment was repeated to produce calibration plots of Log(initial number of cells) versus time of detection using three other substrates for *E. coli* and total coliform detection. FIG. 11B shows *E. coli* detection time at various initial cell counts with the anthracene-β-D-glucuronide substrate. These experiments were conducted with 100 mL samples, stirred at 35° C., using 0.75 mg of substrate, and *E. coli* strain 25922. FIG. 11C shows total coliform detection time at various cell counts using the pyrene-β-D-galactopyranoside substrate. Detection is demonstrated using *E. coli* B-type as the test organism, as *E. coli* is in the coliform class. These experiments were conducted with 10 mL samples stirred at 37° C. FIG. 11D shows total coliform detection time at various cell counts using the anthracenyl-β-D-galactopyranoside substrate. Detection is demonstrated using *E. coli* 25922 as the test organism, as *E. coli* is in the coliform class. These experiments were conducted with 20 mL samples stirred at 37° C.

Example 6

Detection of Four *E. coli* Strains

*E. coli* B (stock No. 413) was obtained from a research group at Queen's University at Kingston, Kingston, Ontario, Canada. Strain ATCC 25922 was purchased from the American Type Culture Collection. Strains KS1 and KS2 were isolated from sewage treatment plant effluent from the City of Kingston, and represent "wild-type" or natural strains.

Figure 12A:
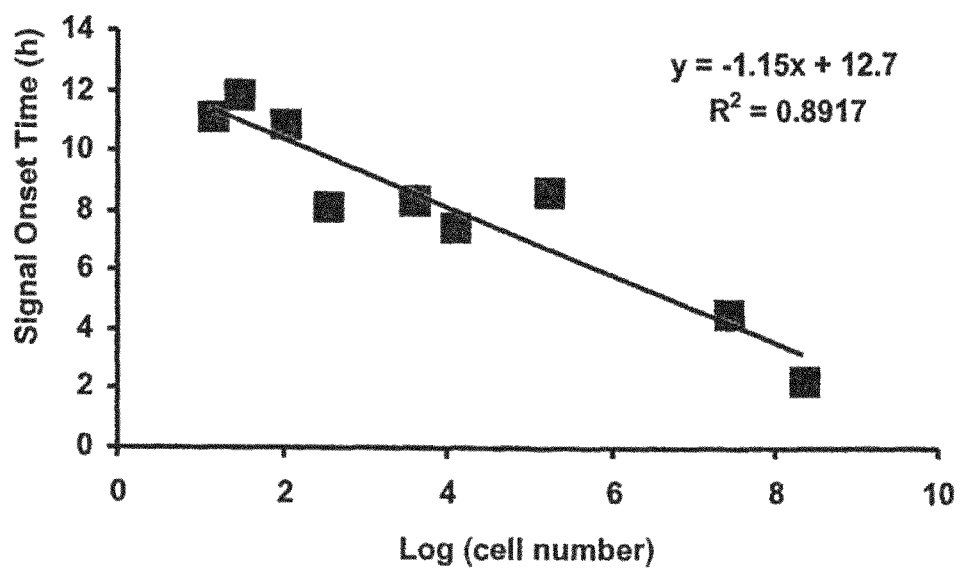
FIGS. 12A and B are plots showing the change in time to detection as a function of cell number for an ATCC strain and a wild-type strain of E. coli, respectively, using an optical probe according to the invention.
Figure 12B:
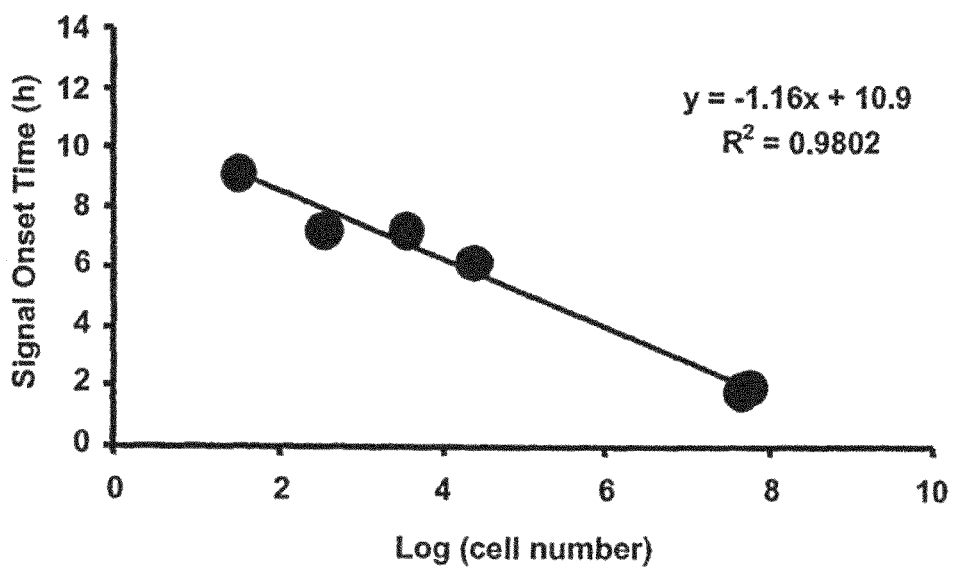

These strains were subjected to the analysis described above; i.e., using the pyr-glu substrate and tracking probe signal vs. time as each strain grew to obtain a "signal onset time", which is related to the number of cells originally present. The results for the ATCC strain and one of the Kingston sewage strains are plotted in FIGS. 12A and B. As can be seen from FIGS. 12A and B, the slopes of all curves are equivalent (representing the change in detection time as a function of change in the log of the number of cells initially present). The y-intercept for these plots predicts the time it would take to detect a single cell in the initial sample.

The fact that the slopes are identical but y-intercepts are slightly different may indicate a difference in a 'lag' or 'resuscitation' time for each strain before growth starts. This places a range of about one order of magnitude on cell count estimates which we can derive from signal onset times for real samples.

Example 7

Anthracene-glucuronide Substrate

The anthracene-β-D-glucuronide (ant-glu) substrate was tested in the same manner as the pyr-glu substrate (above). The ant-glu substrate performed substantially identically to the pyrene substrate. The excitation and emission wavelengths for detection of this substrate are slightly longer, which provides some improvements when using miniature spectrometer components. For example, the ultraviolet light emitting diode used for excitation in some configurations has a maximum output at 375 nm, which is longer than the maximum wavelength for exciting hydroxypyrene (340 nm) but closer to the maximum wavelength for exciting hydroxyanthracene (370 nm).

Example 8

Pyrene-galactopyranoside Substrate for Galactosidase Enzyme

Figure 13A:
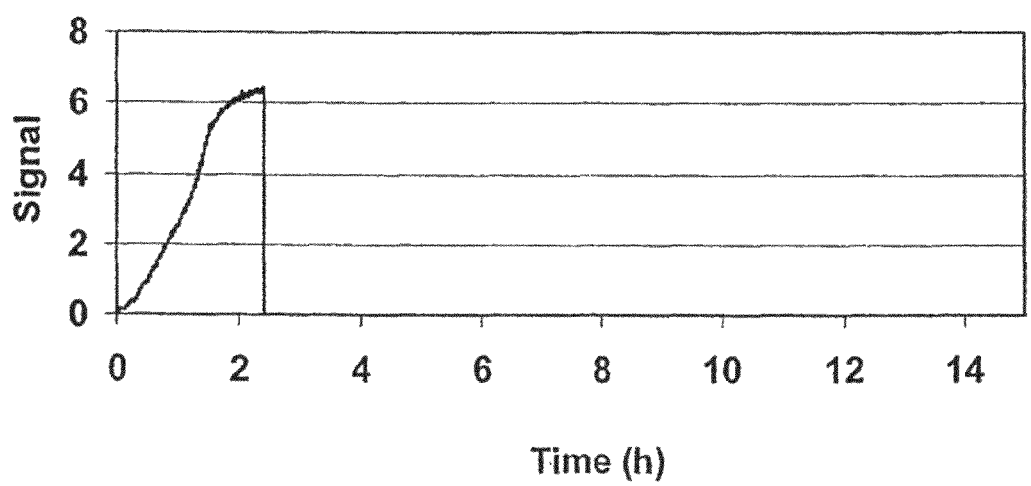
FIGS. 13A and B are plots showing optical probe signal intensity as a function of time, for detection of E. coli in samples containing millions of cells and thousands of cells, respectively.
Figure 13B:
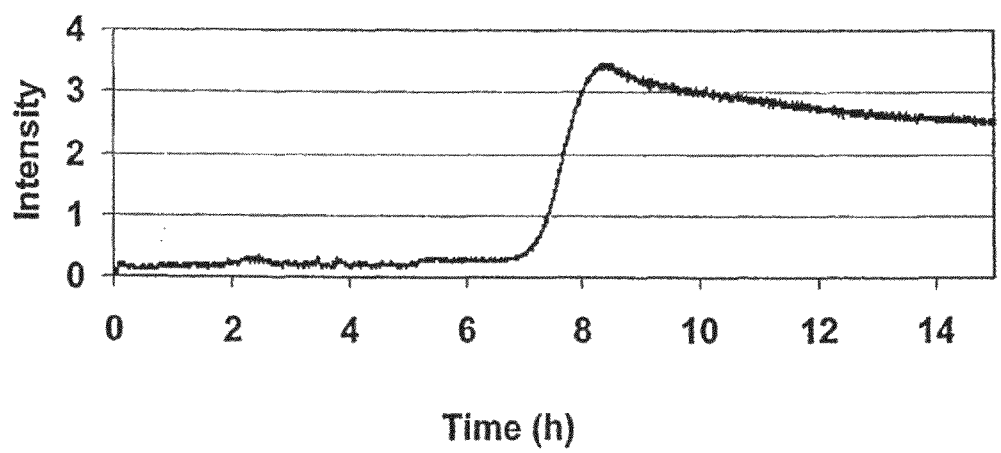

A substrate for detection of galactosidase activity, pyrene-galactopyranoside (pyr-gal), was synthesized and tested with *E. coli* B (stock No. 413). The galactosidase enzyme test is used as an indicator of "total coliform" bacteria, analogous to the glucuronidase test for *E. coli*. Since the product from this substrate is identical to the glucuronidase product, i.e., hydroxypyrene, it was expected that the method and optical probe of the invention would work as well as with the pyr-glu substrate, provided that the galactosidase enzyme was expressed. Initial results for samples estimated to contain millions of cells (FIG. 13A) and a few thousand cells (FIG. 13B) are substantially identical to the glucuronidase test.

Example 9

Comparison of *E. coli* Tests

Water samples (n=37) from local fresh water sources (lakes and rivers) in and near Kingston, Ontario, Canada were delivered to a local accredited laboratory (referred to as Reference Lab) for *E. coli* analysis using a standard membrane filter method. The Reference Lab removed a 10 ml volume from each ~200 ml sample for analysis, and then turned the remaining sample over to the inventors. A 10 ml volume of each sample was mixed with 10 ml of nutrient broth concentrate to provide 20 ml of standard medium (same medium as used in the above *E. coli* work), to which was added the pyr-glu substrate. The samples were placed in a 37° C. bath and a stir bar and the optical probe were added. Fluorescence was monitored, and the "time to detect" ($t_d$) was determined for each sample. Negative samples gave no significant fluorescence signal after at least 20 h.

Figure 14:
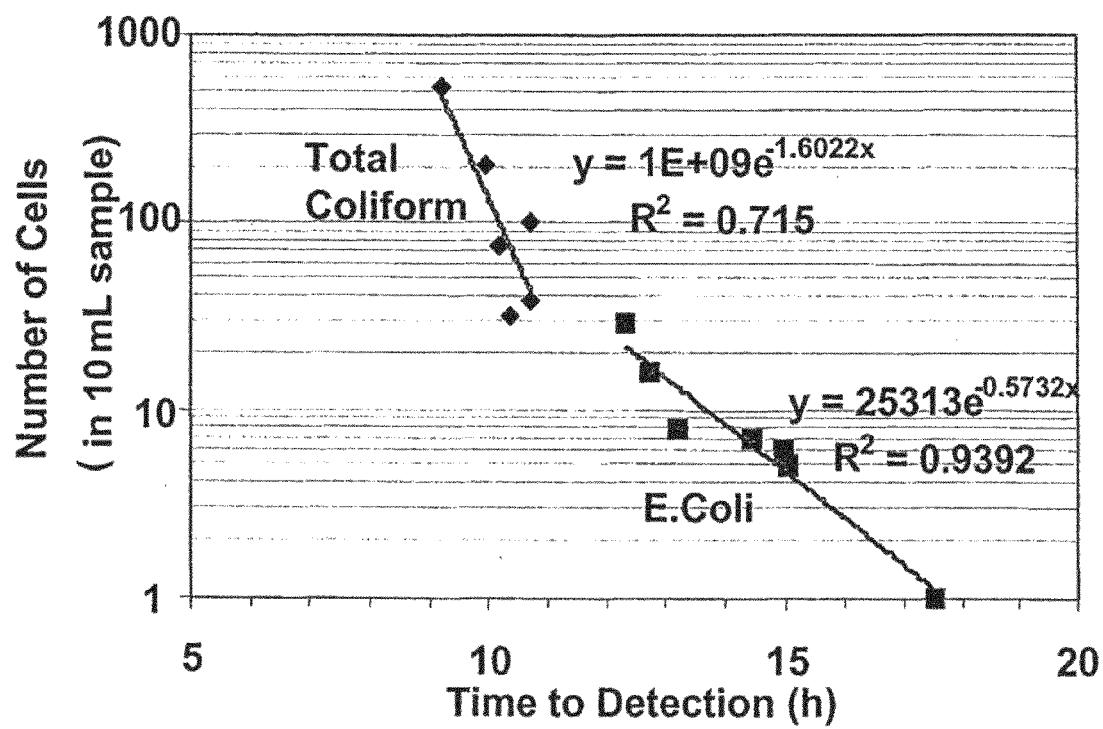
FIG. 14 shows calibration curves for time to detection for E. coli and total coliform, using detection of glucuronidase and galactosidase activity, respectively.

Results for an initial set of these samples were used to calibrate the $t_d$ response, yielding the *E. coli* curve shown in FIG. 14. This calibration was used to convert "colony forming units" or CFUs that are detected by the standard membrane filter subsequent $t_d$ results into "number of cells per unit volume" (which are equivalent to method) for each sample. The results of the comparison indicated good agreement, especially in the 0 to 25 CFU range, between the invention and the standard laboratory technique. In Table 1a qualitative comparison of the two methods is given. Table 1 casts the data into a "presence/absence" format, with allowance for sampling statistical variations at the one-cell level. The comparison indicates perfect agreement between the "positive" and "negative" classification of the samples.

This comparison demonstrates that the invention provides numerous advantages over the Reference Lab technique with no sacrifice in performance. For example, the invention provides a test which: is faster (e.g., less than 15 h, with faster detection for more contaminated samples vs. 18 to 24 h for the Reference Lab test); requires less manipulation of the sample; provides optical detection with no visual counting, observation, or human intervention (and therefore not subjected to human error); can be used in overgrown and/or opaque samples; and has a wide dynamic range (e.g., 1 to $1 \times 10^6$ cells vs. 1 to 100 cells for the Reference Lab) such that no dilutions are necessary.

TABLE 1

Comparison of the invention and Reference Lab technique for detection of *E. coli* in a "presence-absence" mode.

| Comparison of *E. coli* test results. | Number of Occurrances |
|---|---|
| Invention: +ve, Reference Lab: +ve (Confirmed Positives) | 19 |
| Invention: 1 cell, Reference Lab: −ve (Potential false positives) | 1 |
| Invention: >1cell, Reference Lab: −ve (False Positives) | 0 |
| Invention: −ve, Reference Lab: −ve (Confirmed Negatives) | 12 |
| Invention: −ve, Reference Lab: 1 cell (Potential false negatives) | 5 |
| Invention: −ve, Reference Lab: >1 cell (False Negatives) | 0 |
| Total samples | 37 |

Example 10

Detection of Total Coliform

A subset of the samples of Example 9 were selected for total coliform (TC) analysis using the pyr-gal substrate. Since the Reference Lab was not doing total coliform determinations for these, a separate TC test using the commercial Quantitray system (Colilert-18®, Idexx Laboratories Inc., Westbrook, Me.), which provides a TC result using the Most Probable Number (MPN) quantitative method, was also performed on the samples. Initial results are provided in FIG. 13; however, it should be noted that more data is needed to confirm the mathematical values for the log-linear fit of this data. Therefore, it cannot be concluded whether this curve is different from the *E. coli* curve of FIG. 14, as the two cover different contamination ranges. It should be emphasized that both curves use real samples with a random variation in the actual strains of coliform organisms present, so overall performance is expected to be similar to the *E. coli* test.

Example 11

Preparation of 2-anthracenyl-β-D-galactopyranoside

Figure 15:
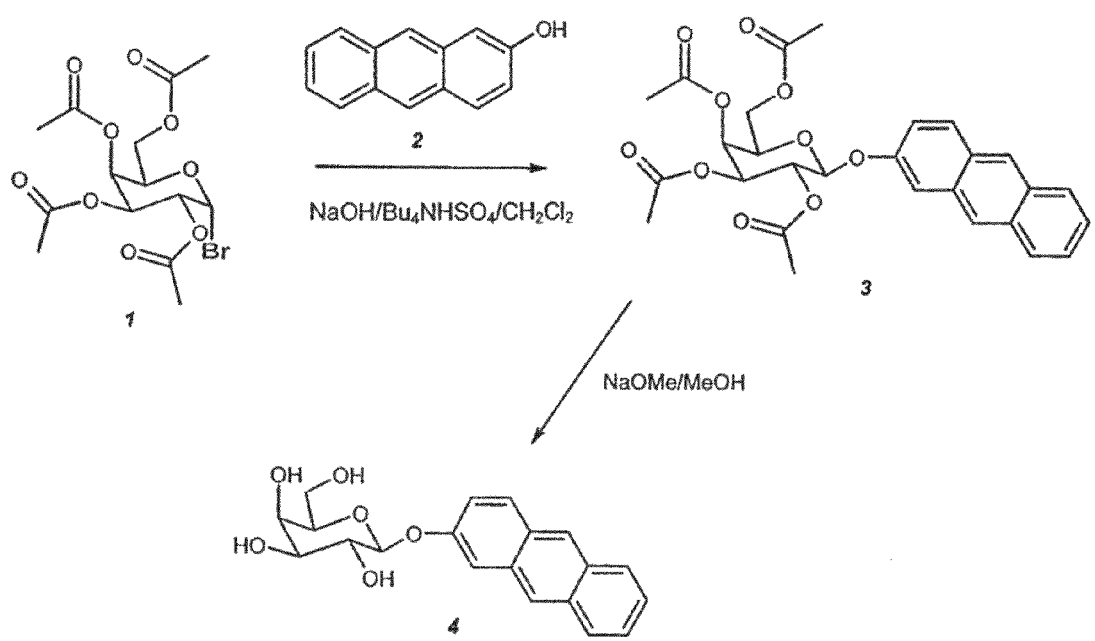
FIG. 15 shows a scheme for synthesizing 2-anthracenyl-β-D-galactopyranoside.

2-Anthracenyl-β-D-galactopyranoside 4 was prepared according to the scheme shown in FIG. 15. Glycosylation of 2-hydroxyanthracene 2 under phase transfer conditions (11) with acetobromogalactose 1 gave good yields of conjugate 3 which was deprotected to 4 under Zemplen conditions.

Example 12

Preparation of 1-pyrenyl-β-D-galactopyranoside

Figure 16:
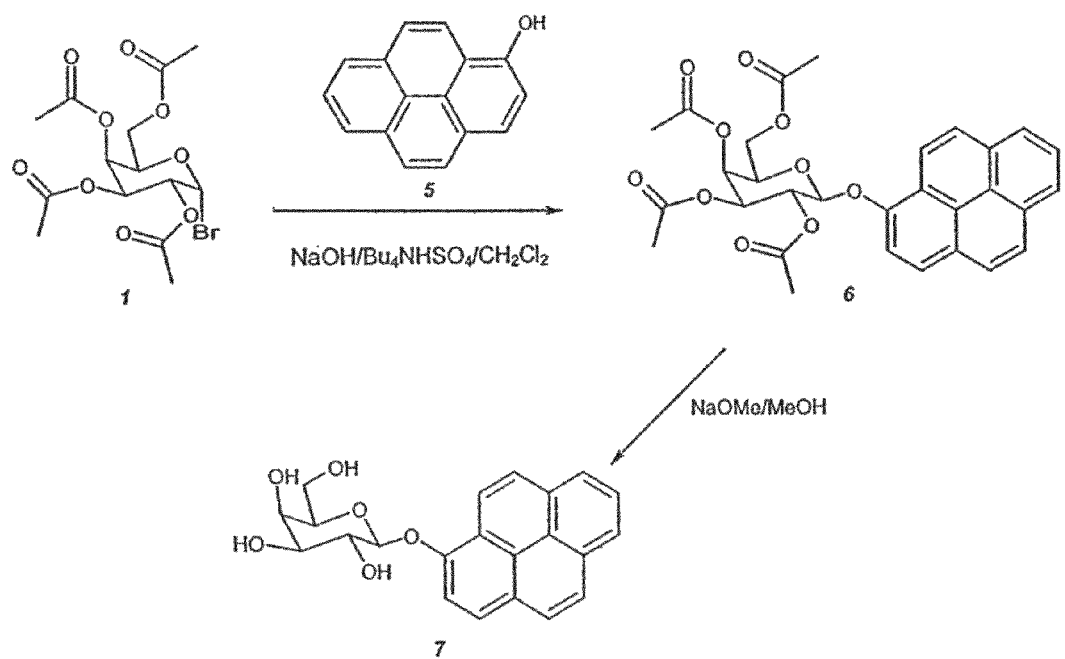
FIG. 16 shows a scheme for synthesizing 1-pyrenyl-β-D-galactopyranoside.

1-Pyrenyl-β-D-galactopyranoside 7 was prepared in similar fashion to that of Example 11 from 1-hydroxypyrene and acetobromogalactose (scheme shown in FIG. 16).

Figure 17:
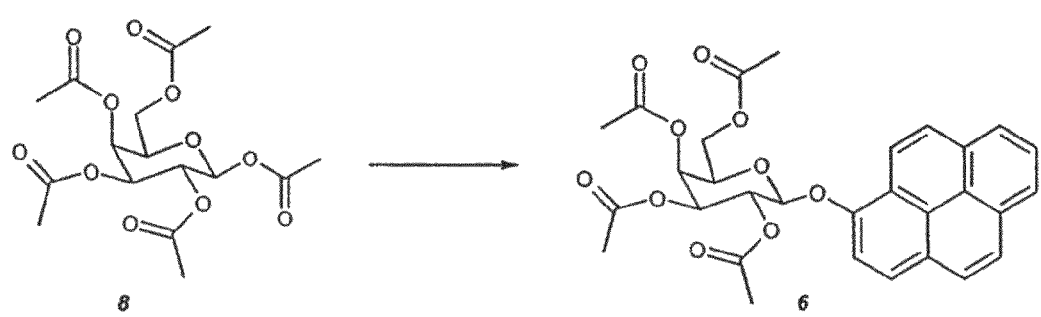
FIG. 17 shows an alternative scheme for glycosylation of 2-hydroxyanthracene and 1-hydroxypyrene.

As shown in FIG. 17, glycosylation of 2-hydroxyanthracene and 1-hydroxypyrene may also be effected by fusing the aglycone with penta-acetyl galactose 6(12) but the yields of conjugate 6 are not high.

Example 13

Preparation of anthracene-β-D-glucuronide

Figure 18:
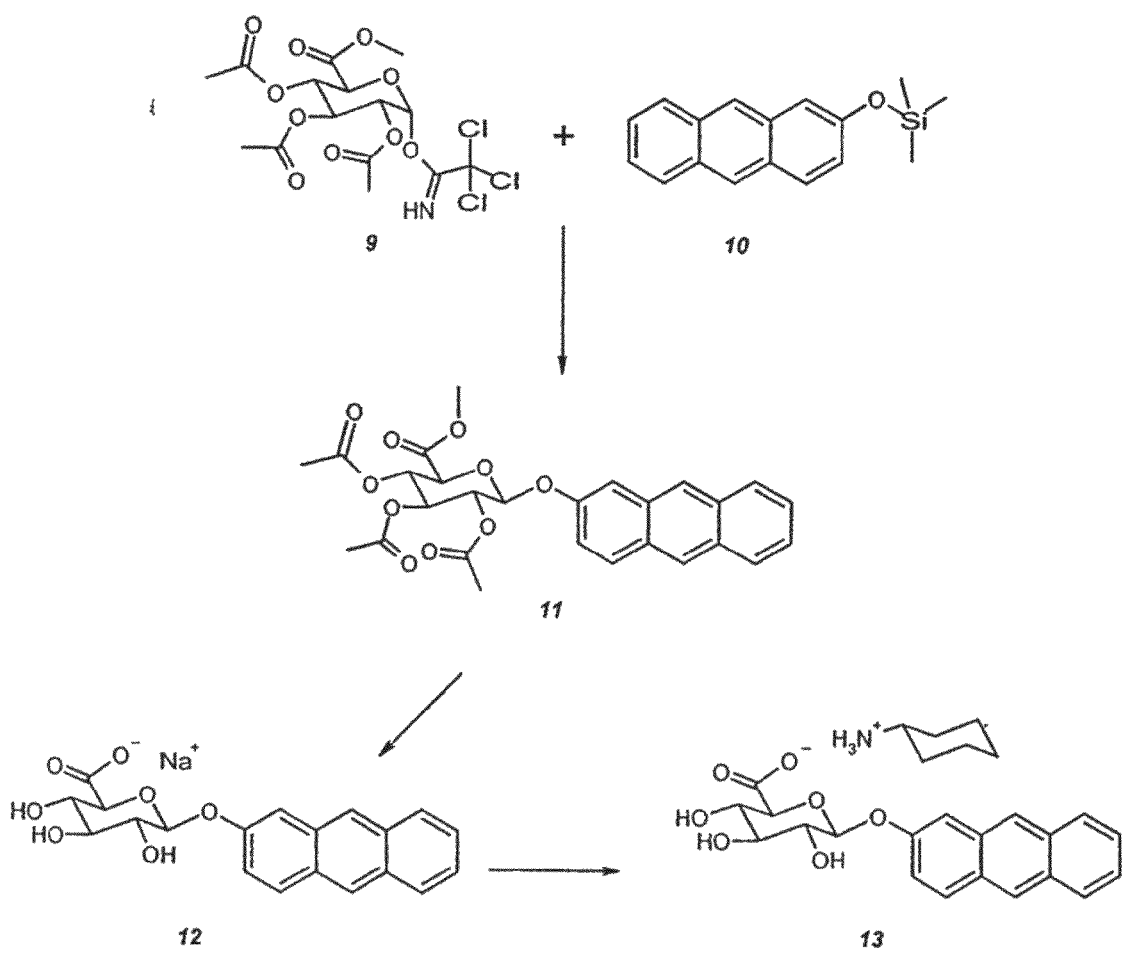
FIG. 18 shows a scheme for preparing anthracene glucuronide.

Anthracene-β-D-glucuronide was prepared according to the scheme shown in FIG. 18. 2-Hydroxyanthracene was converted to the trimethylsilyl ether 10 to increase its solubility. The trimethylsilyl ether 10 was coupled to the trichloroacetamidate 9 (13) in the presence of boron trifluoride etherate. Deprotection of the resultant conjugate 11 with sodium methoxide in dry methanol followed by the addition of water allowed the sodium salt 12 to crystallize from solution. This salt may be changed to the cyclohexylammonium salt 13 by salt exchange with cyclohexylammonium acetate.

Figure 19:
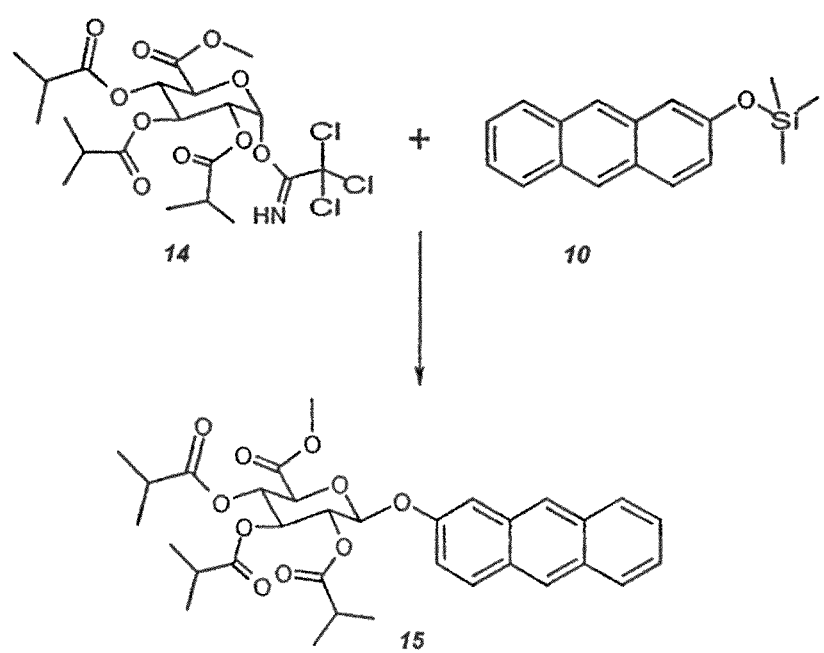
FIG. 19 shows an alternative scheme for preparing the glucuronide of anthracene.

The isobutyryl trichloroacetamidate 14 (15) may also be used to prepare the glucuronide of anthracene via the conjugate 15, as shown in the scheme of FIG. 19, but the yields are not improved.

Example 14

Preparation of 2-anthracenyl-β-D-galactopyranoside 4

Preparation of tetra-O-acetyl-2-anthracenyl-β-D-galactopyranoside 3

A mixture of tetra-O-acetyl-1-bromo-1-deoxygalactose 1 (205 mg, 0.5 mmole), 2-hydroxyanthracene 2 (74 mg, 0.381 mmole), tetrabutylammonium hydrogen sulfate (100 mg, 0.294 mmole), dichloromethane (2.5 mL) and 1.5 M sodium hydroxide (0.5 mL, 0.75 mmole) was stirred vigorously at room temperature overnight. The reaction mixture was diluted with ethyl acetate (20 mL), washed with water (3×10 mL), satd brine (10 mL) and dried with sodium sulfate (×2). Evaporation of the solvent gave a brown gum (249 mg) which was chromatographed on silica gel using dichloromethane followed by 39/1 dichloromethane/ethyl acetate as eluant to give compound 3 as a golden foam (129 mg, 65% yield).

$^1$Hmr (CDCl$_3$, δ): 2.06 (3H, s, OAc), 2.12 (6H, s, OAc), 2.22 (3H, s, OAc), 4.23 (3H, m, H$_{5'}$ and H$_{6'}$), 5.20 (1H, q, j=3.0, 10.4 Hz, H$_{3'}$), 5.24 (1H, d, j=8.0 Hz, H$_1$'), 5.52 (1H, d, j=3.0 Hz, H$_{4'}$), 5.60 (1H, q, j=8.0, 10.4 Hz, H$_{2'}$), 7.22 (1H, q, j=2.4, 9.1 Hz, H$_3$), 7.48 (3H, m, H$_1$, H), 7.99 (3H, m,), 8.33 (1H, s, H$_9$), 8.41 (1H, s, H$_{10}$).

A solution of tetra-O-acetyl-2-anthracenyl-β-D-galactopyranoside 3 (30 mg, 0.057 mmole) in dry methanol (0.6 mL) was stirred at room temperature and treated with 0.052 M sodium methoxide in methanol (100 μL, 0.0052 mmole). After 20 min a white precipitate began to form. After stirring overnight the product was filtered and washed with a little methanol then sucked dry to leave a creamy white solid, 14.8 mg (72.5%).

$^1$Hmr (DMSOd$_6$, δ): 3.4-3.8 (6H, m), 4.53 (1H, d, j=4.2 Hz, OH), 4.71 (1H, t, j=5.5 Hz, primary OH), 4.88 (1H, d, j=5.7 Hz, OH), 5.06 (1H, d, j=7.7 Hz, H$_{1'}$), 5.22 (1H, d, j=5.1 Hz, OH), 7.30 (1H, q, j=1.8, 9.4 Hz, H3), 7.48 (2H, m, H$_6$, H$_8$), 7.57 (1H, br. d, H$_1$), 8.04 (3H, m, H$_4$, H$_5$, H$_7$), 8.40 (1H, s, H$_9$), 8.53 (1H, s, H$_{10}$).

Example 15

Preparation of 1-pyrenyl-β-D-galactopyranoside

1-Pyrenyl-β-D-galactopyranoside was prepared in similar fashion to that described in Example 14.

$^1$Hmr (DMSOd$_6$, δ): 3.4-3.95 (6H, m), 4.62 (1H, d, j=4.6 Hz, OH), 4.72 (1H, t, j=5.5 Hz, primary OH), 4.97 (1H, d, j=5.6 Hz, OH), 5.17 (1H, d, j=7.6 Hz, H$_{1'}$), 5.47 (1H, d, j=5.4 Hz, OH), 7.91 (1H, d, j=6.5 Hz), 8.00-8.18 (4H, m), 8.18-8.30 (3H, m), 8.57 (1H, d, j=9.2 Hz).

Tlc (10/1 ethyl acetate/methanol, UV) showed a single spot Rf 0.14.

Example 16

Preparation of methyl tri-O-acetyl-2-anthracenyl-β-D-glucuronide 11

Preparation of 2-hydroxyanthracene trimethylsilyl ether 10

To a solution of 2-hydroxyanthracene (14) (100 mg, 0.515 mmole) in dry pyridine (1.0 mL) was added chlorotrimethylsilane (120 μL, 0.845 mmole). A precipitate formed immediately. After stirring overnight at room temperature, toluene (3 mL) was added and the mixture filtered. The solids were washed with more toluene and the combined filtrates were stripped down to leave an orange crystalline solid. The residue was dissolved in toluene (5 mL) and again filtered to remove a trace of pyridine hydrochloride. Evaporation of the solvent afforded an orange solid which was dried under high vac to give a quantitative yield (140 mg) of the trimethylsilyl ether, which was used below without purification.

A 25 mL pear shaped flask was charged with 2-hydroxyanthracene trimethylsilyl ether 10 (191 mg, 0.717 mmole) and imidate 9 (479 mg, 1.0 mmole) and flushed with nitrogen. Powdered, activated 3 Å molecular sieves (1.0 g) were added quickly to the reaction flask which was again flushed with nitrogen and cooled in ice. Dry dichloromethane (8.5 mL) was added and the mixture was stirred for 30 min. with ice cooling. Boron trifluoride etherate (85 μL, 0.67 mmole) was finally added and the reaction immediately turned a grey green colour. The reaction mixture was stirred overnight under nitrogen and allowed to warm slowly to room temperature.

The reaction was quenched by adding methanol (2 mL) and stirring for 10 min. The solids were filtered off and washed well with dichloromethane. The combined filtrates were evaporated to leave a brown foam which was dissolved in dichloromethane and treated with silica gel (1 g) and re-evaporated. The residue was added to the top of a silica gel column (20 g) prepared in dichloromethane which was eluted with this solvent. The fractions containing the product were combined and evaporated to leave a dirty yellow solid, (152 mg). Crystallization from ethyl acetate (2.0 mL) gave an off white solid (69 mg, 19%).

$^1$Hmr (CDCl$_3$, δ): 2.10 (9H, m, 3×OAc), 3.76 (3H, s, OCH$_3$), 4.33 (1H, m, H$_{5'}$), 5.41 (4H, m), 7.21 (1H, q, j=2.5, 9.0 Hz, H3), 7.49 (3H, m, H$_6$, H$_8$, H$_1$), 7.98 (3H, m, H$_4$, H$_5$, H$_7$), 8.35 (1H, s, H$_9$), 8.40 (1H, s, H$_{10}$).

Example 17

Preparation of 2-anthracenyl-β-D-glucuronic acid, sodium salt 12

Methyl tri-O-acetyl-2-anthracenyl-β-D-glucuronide 11 (145 mg, 0.284 mmole) was suspended in dry methanol (4.0 mL) and cooled in an ice bath under nitrogen. To this was added 0.678 M sodium methoxide solution (710 μL, 0.48 mmole). The mixture was stirred overnight, allowing to warm slowly to room temperature. The solid was slowly consumed as the product precipitated from solution. The following day water (1.0 mL) was added and stirring at room temperature continued. The fine precipitate was filtered, washed with a little methanol and sucked dry to give the product as an off white solid (97 mg, 87%).

$^1$Hmr (D$_2$O, δ): 3.61 (3H, m), 3.76 (1H, d, j=8.4 Hz, H$_{5'}$), 5.25 (1H, br. d, j=4.6 Hz, H$_{1'}$), 7.62 (1H, br. d, j=9.0 Hz, H$_3$), 7.45 (2H, m, H$_6$, H$_8$), 7.54 (1H, br. d, H$_1$), 7.98 (3H, m, H$_4$, H$_5$, H$_7$), 8.36 (1H, s, H$_9$), 8.43 (1H, s, H$_{10}$). $^1$Hmr (DMSOd$_6$, δ): 5.07 (1H, d, j=7.5 Hz, H$_{1'}$).

Example 18

Preparation of 2-anthracenyl-β-D-glucuronic acid, cyclohexylammonium salt 13

The sodium salt 12 (54 mg, 0.137 mmole) was suspended in methanol (~5 mL) and water (3 mL) and heated to boiling. The solution was filtered through a tissue plug contained in a Pasteur pipette and washed through with hot water (0.5 mL). To the hot filtrate was added cyclohexylammonium acetate (22 mg, 0.138 mmole) and the resultant solution was stirred as it cooled. When cooled in ice the cyclohexylammonium salt crystallized which was harvested by filtration as a buff solid (39.7 mg, 62%).

$^1$Hmr (DMSO-d$_6$, δ): 1.19 (5H, m), 1.5-1.9 (5H, m), 2.87 (1H, m, H$_{1''}$), 3.62 (1H, d, j=9.8 Hz, H$_{5'}$), 5.11 (1H, d, j=6.9 Hz, H$_{1'}$), 7.29 (1H, q, j=1.9, 9.1 Hz, H$_3$), 7.47 (2H, m, H$_6$, H$_8$), 7.55 (1H, br. d, H$_1$), 8.04 (3H, m, H$_4$, H$_5$, H$_7$), 8.41 (1H, s, H$_9$), 8.52 (1H, s, H$_{10}$).

Example 19

Preparation and Evaluation of a Polymer Sphere Partitioning Element Optical Probe This example describes the preparation and evaluation of a silicone or polydimethylsiloxane (PDMS) sphere partitioning element optical probe.

PDMS has a neutral polarity, which makes it hydrophobic. This property causes the material to form a compact shape, i.e., a sphere, when immersed in water. The PDMS used for the partitioning element described in this example is slightly more dense than water, so a sphere of the material will sink to the bottom of an aqueous solution and adhere to the bottom surface of the vial. As the material cures into a rigid polymer, its density increases slightly. We have developed a scheme which uses a polar batch solution with a density gradient such that a sphere remains buoyant long enough to cure while suspended.

The batch solution was prepared as follows. A solution of 1.4 g. of sodium acetate trihydrate and 4 mL of water was prepared by thoroughly mixing in a 20 mL glass vial. 4 mL of 95% ethanol was then added slowly to the same vial without any agitation. The sodium acetate layer is highly polar and more dense than the PDMS material and cured silicone, while the alcohol layer is relatively polar but less dense than the precursor material. Once immersed in the solution, the sphere of polymer material moves quickly towards the mixed layer between the two discrete layers and remains suspended there. The sphere does not move laterally in the mixed layer, so it is possible to produce numerous spheres in a single vial by injecting PDMS material into the solution.

The batch solution assures an identical shape for each sphere, but the size of the sphere depends on the amount of injected PDMS material. Standard lab pipettes and syringes cannot be used for accurate volume injections due to the high viscosity of the precursor silicone. Therefore, a solvent is added to the precursor material to reduce its viscosity. During the curing phase of the polymer, the solvent simply diffuses or evaporates away. Numerous solvents such as dichloromethane, hexane and other organics can be used to dissolve the precursor material; however, these solvents are not fully miscible in ethanol or water and will cause the silicone to slowly rise to the surface of the batch solution upon curing. Tetrahydrofuran (THF) is a solvent that can dissolve the precursor material and slowly dissipate into the ethanol, leaving the silicone sphere in the mixing layer of the batch solution for a 90 to 100% production yield. The amount of THF required for reproducible injections varies with the type and brand of silicone used. For a sphere mass of about 1.2 mg (diameter of about 1.5 mm), 0.45 mL of THF per gram of silicone precursor is required when using Dow Corning Sylguard 184 silicone, and 0.6 mL of THF per gram of silicone is required when using United Chemical Technologies silicone.

Calibrated pipettes and syringes can be used to inject the silicone/solvent into the batch solution. Better reproducibility was obtained using syringes when preparing 1 mg to 3 mg spheres. When using a syringe, the gauge on the syringe barrel can conveniently be used to set the volume of silicone/solvent solution injected into the batch solution. Once the polymer/solvent is loaded into the syringe, the needle is wiped clean and inserted into the ethanol layer of the batch solution. The needle plunger is slowly pressed until a drop of the polymer solution releases itself from the needle and quickly drops to the boundary layer of the batch solution where it remains. The needle is moved to another location in the ethanol layer and another drop is squeezed out of the needle. In this way, about a dozen spheres can be produced in a 20 ml vial. The syringe is carefully removed from the batch solution and the vial is then capped and left still at room temperature until the curing period has elapsed.

To remove the solid polymer spheres from the batch solution, a plastic filter funnel with pore size smaller than the spheres is used to filter the batch solution. The retained spheres are then washed with 95% ethanol to remove any residual sodium acetate and left to dry. When dry, the polymer spheres are weighed and sorted by mass.

Performance of the Polymer Sphere Partitioning Element Optical Probe

The batch process used to mass-produce polymer sphere partitioning elements as described above assures that the silicone spheres have consistent size, morphology, and optical clarity, which improves the detection limit of the optical probe. As a result, equilibration time, signal production in a given product solution, such as hydroxypyrene or hydroxyanthracene, and calibration of optical probes made with the spheres is standardized As noted above, various PDMS formulations can be used in the preparation of silicone spheres. The various formulations change the physical properties of the polymer. For example, Dow Corning Sylgard 184 produces a very rigid polymer due to a high degree of cross-linking and the addition of filler materials such as fumed silica. This polymer has an extremely long life in solution due to its ability to withstand degradation and minimize swelling in alcohol solutions. The disadvantage of this formulation is that 1 mg spheres require 3 hours to equilibrate in a product solution. A 1 mg sphere produced from United Chemical Technologies silicone equilibrates in 1 hour. This sphere is less rigid than a sphere produced with Sylguard 184 due to the lack of fumed silica and a lower degree of cross-linking; however, it is more susceptible to swelling and degradation. The degree of cross linking can be controlled in both formulations to achieve a polymer that has an equilibration time of between 1 and 3 hours, as shown in Table 2.

TABLE 2

Formulations of two brands of PDMS materials to produce spheres.

| Equilibration Time per mg | PDMS | Formulation |
|---|---|---|
| 3 hours | Dow Corning Sylguard 184 | Mix 10:1 by weight of base silicone elastomer to curing agent |
| 1 hour | United Chemical Technologies PS443/PS123 | Mix 38:1 by weight of base (PS443) to cross-linker (PS123) |

Example 20

Enzyme Immunoassay Using Optical Probe

Introduction

This example describes use of an optical probe with a PDMS partitioning element as described above in an immunoassay for detection of 17-β-estradiol (E2). A standard immunoassay kit was used for this purpose. Assay Designs' Correlate-EIA 17-β-Estradiol kit (Assay Designs Inc., Ann Arbor, Mich.) is a competitive immunoassay for the quantitative determination of E2 in biological and environmental samples. The standard or conventional assay procedure is described as follows:

A sample or standard solution which may contain E2 is placed in a microwell in a microtitre plate along with a second solution containing E2 which is attached to an alkaline phosphatase (AP) enzyme label (AP-E2). Polyclonal antibody to E2 (anti-E2) is added to the microwell, which has been previously coated with another antibody which binds the anti-E2 irreversibly to the microwell surface. Relative to the number of immobilized antibody molecules, excess AP-E2 is added. Competitive binding of both E2 and AP-E2 occurs, resulting in an immobilized amount of AP-E2 which is inversely related to the amount of E2 in the mixture. After a binding period, residual sample and reagents are washed away leaving only immobilized AP-E2 and E2 antibody complexes in the microwell. A solution of substrate is added to determine the amount of AP-E2 immobilized through an enzyme activity measurement. A reaction between the substrate and AP to produce a coloured product is monitored. The commercial kit normally uses p-nitrophenylphosphate as the substrate, with p-nitrophenol as the product.

To quantitate the enzyme activity, the yellow colour generated is measured as absorbance at 405 nm either continuously (providing an absorbance vs. time curve) or after a fixed (e.g., 20 min) incubation time. The "signal" monitored is the slope of the absorbance vs. time curve or value of the absorbance measured in the fixed-time mode. The signal is maximal for a blank containing only AP-E2, and decreases with increases in E2 levels in the sample. The signal for any sample relative to the signal for a blank solution is a measure of the relative binding of AP-E2, and is often expressed as a fraction or percentage bound. A plot of fraction bound vs. E2 concentration for standard solutions provides a calibration curve for the assay, which is then used to determine concentrations in unknown samples.

The detection instrument used in such immunoassay is normally a "bench-top" microtitre plate reader. This is a sophisticated and expensive (~$30,000) instrument requiring some expertise to operate, and costly maintenance. Alternatively, conventional spectrometers with "microplate" attachments can be used. Other immunoassays are done in larger vessels (e.g., 5 mL test-tube configuration) with detection in a bench-top or even portable spectrometer, though these use larger sample volumes, more reagents per sample and hence operate at a higher cost. The portable or field versions usually have poorer precision and detection limits. Other portable immunoassays use "test strips" with visual read-out, but these normally cannot provide quantitative results and have poorer detection limits.

Here we describe an alternative detection scheme for standard enzyme immunoassays using an optical probe for detecting enzyme activity. This can be used in the competitive binding scheme described above and in all other enzyme immunoassay schemes, including "sandwich" assays, "immunoprobes" and immunolabelling systems.

In our approach, we use an optical probe having a polymer partitioning element (see Examples 1 and 19, above) for detection of the product. For monitoring AP activity, a substrate with a phosphate moiety attached to a fluorescent compound is used, where the product fluorescent compound is one which will be detected with the optical probe. For demonstration of this approach, we synthesized 1-pyrenephosphate (PP), which on reaction with AP produces 1-hydroxypyrene (HOP), which is efficiently detected by the partitioning element of the optical probe, and phosphate ion.

In our assay, the optical probe is inserted into the microwell containing bound AP (i.e., AP-E2) and PP substrate. As reaction between PP and AP produces HOP, the HOP is detected by the probe. As in the conventional assay, HOP can be detected continuously (probe inserted before or with PP) or in "endpoint" mode (PP conversion to HOP stopped at a fixed reaction time and then probe inserted). The signal in either case is the slope of a fluorescence vs. time curve, and a calibration plot is generated using a similar approach to that described above for the conventional immunoassay.

Experimental

Chemicals and Reagants

Assay Designs' Correlate-EIA 17-β-Estradiol kit (Catalogue No. 901-008) was bought from Assay Designs Inc. (Ann Arbor, Mich.). Tris[hydroxymethyl]aminomethane (tris) and $MgCl_2 \cdot 6H_2O$ were obtained from Sigma-Aldrich (Mississauga, Ontario, Canada). 0.1 M Tris buffer pH 9 with 1.0 mM $MgCl_2$ was prepared fresh everyday. 1-Pyrenephosphate was synthesized in our lab. Substrate stock $4.97e^{-4}$ M was prepared in pH 9 0.1 M tris-HCl buffer with 1.0 mM $MgCl_2$ immediately before use. 2M sulphuric acid (Fisher Scientific, Ottawa, Ontario, Canada) was used as stop solution.

Instrumentation

Fluorescence measurements were made using a spectrometer (Sciencetech Inc., London, Ontario, Canada) with a 75 watt xenon arc lamp and photomultiplier detector. Excitation and emission slits were set to 5 nm band-pass for all measurements. Excitation wavelength was 345 nm and emission wavelength was 385 nm. An optical probe with polymer partitioning element (see Examples 1 and 19) was used with an optical probe coupling system for product detection (see, e.g., FIG. 3A).

Procedure

Immunoassay was carried out following the manufacturer's recommended procedure. Reactions were carried out in microwells coated with antibody. All assays were done at room temperature (24±2° C.). All reagents were brought to room temperature for at least 30 minutes prior to opening. 100 µl assay buffer was pipetted into the Bo microwell and 100 µl of standards #1 through #6 were added into individual wells. 50 µl conjugate and 50 µl antibody were then added to each well in "endpoint" mode immunoassay. For kinetic mode immunoassay, 20 µl conjugate and 20 µl antibody were added and assay buffer was also added to each well to make up the volume 60 µl. The plate was covered with a plate sealer and incubated for 2 hours at with orbital shaking at ~500 rpm. After incubation, the plate was washed 4 times with 300 µl/well wash solution.

After washing out unreacted reagents, 250 µl of buffered PP solution was added to the wells. In the continuous immunoassay, the optical probe was inserted before or with the PP solution. In the endpoint immunoassay, after 30 min incubation at room temperature the PP conversion reaction was stopped with 50 µl of 2M $H_2SO_4$, then the optical probe was inserted into the solution. In either case, the HOP uptake curve was recoded until a reliable slope was obtained. After each assay, HOP was cleaned from the polymer partitioning element of the optical probe with either a 50/50 (v/v) ethanol/water solution or a 1 M NaOH solution.

Results and Discussion

Determination of Parameters $K_M$ and $v_{max}$

Figure 20:
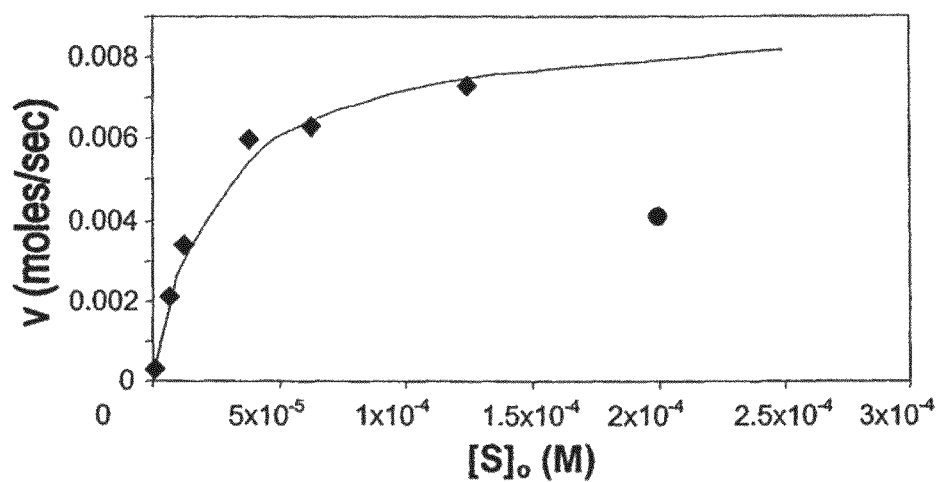
FIG. 20 is a plot showing rate of substrate conversion (v) vs. initial 1-pyrenephosphate (PP) substrate concentration ([S]) for an immunoassay for the detection of 17-β-estradiol using an optical probe according to the invention. Values for v were obtained from the slope of a plot of optical probe signal vs. time, for various initial PP substrate concentrations, after 1000 seconds. The data point at $2\times10^{-4}$ M shows inhibition and was omitted from further analysis. The curved line was drawn using best-fit Michaelis-Menton kinetic parameters (see Example 20)

The Michaelis-Menten kinetic parameters for detection of AP activity were determined since PP has not been previously reported as a substrate for this enzyme. The rate of substrate conversion as a function of substrate concentration was determined by generating a set of optical probe signal vs. time curves. The rates were plotted as a function of substrate concentration (see FIG. 20), and nonlinear curve fitting gave the kinetic parameters $v_{max}=9\times10^{-3}$ moles/s and $K_M=2.45\times10^{-5}$ M. Ideally, a working substrate concentration of the assay of about $10\times K_M$ would be used in assays to maximize sensitivity and slope reproducibility. Since PP inhibition of enzyme activity is indicated at the $2\times10^{-4}$ M level, we decided to use the maximum reliable concentration of $5\times K_M$ ($1.25\times10^{-4}$ M) for further assays using PP.

Immunoassay with Optical Probe

Figure 21:
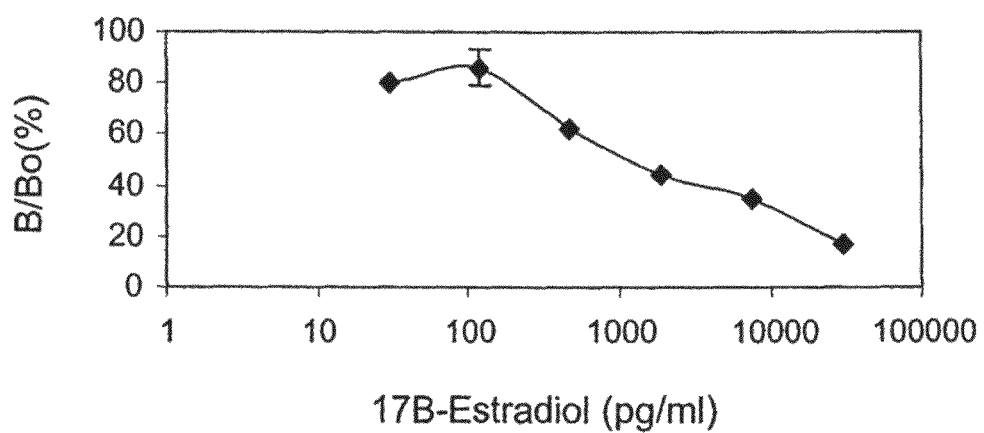
FIG. 21 is an immunoassay binding curve for 17-β-estradiol determination in endpoint mode. B and Bo values were determined from the slope of a plot of optical probe signal vs. time, for various initial PP substrate concentrations, after 2400 seconds. The error bar on the data point at 100 pg/mL was estimated from duplicate runs.

Immunoassay was carried out using $1.25\times10^{-4}$ M substrate solution in pH 9 buffer in endpoint mode. Optical probe responses after immersion in the stop-time solution were obtained. As expected, samples with greater E2 concentration yielded lower bound E2-AP amounts, and hence lower optical probe responses. Relative responses were used to calculate the % Bound E2-AP. The plot of % Bound vs. E2 concentration, which is essentially the calibration curve for the assay, is given in FIG. 21.

Figure 22:
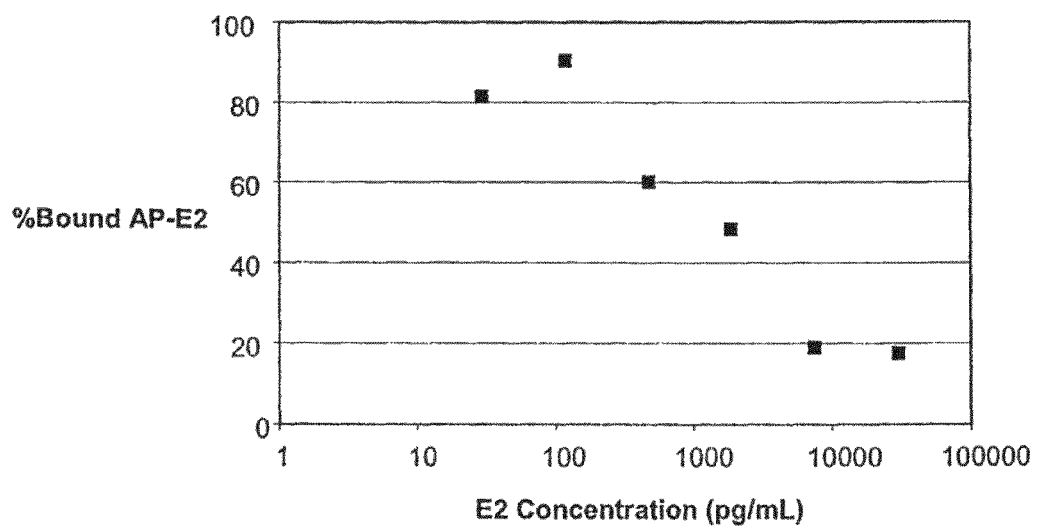
FIG. 22 is an immunoassay binding curve for E17-β-estradiol determination in kinetic mode. B and Bo values were determined from the slope of a plot of optical probe signal vs. time, for various initial PP substrate concentrations, after 5000 to 6000 seconds.

The same immunoassay parameters were used in kinetic mode to generate a plot of optical probe signal vs. time. This data was acquired with an optical probe as described in Example 19, and used to generate the % Bound curve shown in FIG. 22.

Conclusion

These results indicate that this new enzyme immunoassay method using an optical probe to detect enzyme activity produces results comparable to conventional enzyme immunoassay methods, without the need for expensive detection equipment.

Equivalents

Those skilled in the art will recognize, or be able to ascertain through routine experimentation, variants of the embodiments described above. Such variants are within the scope of the invention and are within the scope of the appended claims.

References

1. Manafi, M.; Kneifel, W.; Bascomb, S. Fluorogenic and chromogenic substrates used in bacterial diagnostics. *Microbiology Review* 55:335-348 (1991).
2. Frampton, E. W.; Restaino, L. Methods for *Escherichia coli* identification in food, water and clinical samples based on beta-glucuronidase detection. *Journal of Applied Bacteriology* 74:223-233 (1993).
3. Alonso, J. L.; Soriano, K.; Amoros, I.; Ferrus, M. A. Quantitative determination of *E. coli* and fecal coliforms in water using a chromogenic medium. *Journal of Environmental Science and Health* Part A 33:1229-1248 (1998)
4. Davies, C. M.; Apte, S. C. Rapid enzymatic detection of faecal pollution. *Water Science and Technology* 34:169-171 (1996).
5. Davies, C. M.; Apte, S. C. Field evaluation of a rapid portable test for monitoring fecal coliforms in coastal waters. *Environmental Toxicology* 14:355-359 (1999).
6. d'Auriac, M. B. A.; Roberts, H.; Shaw, T.; Sirevag, R.; Hermansen, L. F.; Berg, J. D. Field evaluation of a semi-automated method for rapid and simple analysis of recreational water microbiological quality. *Applied and Environmental Microbiology* 66:4401-4407 (2000).
7. Nelis, H.; Van Poucke, S. Enzymatic detection of coliforms and *Escherichia coli* within 4 hours. *Water Air and Soil Pollution* 123:43-52 (2000).
8. Robertson, W.; Palmateer, G.; Aldom, J.; Van Bakel, D. Evaluation of a rapid method for *E. coli* and thermotolerant coliforms in recreational waters. *Water Science and Technology* 38:87-90 (1998).
9. Flowers; Daniel G.; Sternfeld, Marvin. Chromogenic compounds and methods of using same. U.S. Pat. No. 5,364,767 (1994).
10. Ley, A. N.; Bowers, R. J.; Wolfe, S. Indoxyl-β-D-glucuronide, a novel chromogenic reagent for specific detection and enumeration of *Escherichia coli* in environmental samples. *Canadian Journal of Microbiology* 34:690-693 (1988).
11. Kleine, H. P.; Weinberg, D. V.; Kaufman, R. J.; Sidhu, R. S. *Carbohydrate Res.* 142:333 (1985).
12. Helferich, B.; Schmitz-Hillbrecht, E. *Ber. Dtsch. Chem. Ges.* 66:378 (1933).
13. Fischer, B.; Nudelman, A.; Ruse, M.; Herzig, J.; Gottlieb, H. E.; Keinan, E. *J. Org. Chem.* 49:4988-4993 (1984).
14. Hall, J.; Perkin A. G. *J. Chem. Soc.* p. 2029 (1923).
15. Schienmann, F.; Lumbard, W. K.; Brown, R. T.; Mayalarp, S. P. International Patent Application No. WO 93/3051 (1993).

We claim:

1. A method for detecting a microorganism in a sample, comprising:
    combining the sample with at least one substrate such that an enzyme of the microorganism can react with the at least one substrate to produce a biological molecule;
    providing a partitioning element that allows partitioning of substantially only the at least one substrate or the biological molecule thereinto in accordance with a partitioning constant ($K_{fs}$); and
    detecting fluorescence of the at least one substrate or the biological molecule in the partitioning element;
    wherein the detected fluorescence indicates the microorganism is present in the sample.

2. The method of claim 1, wherein the partitioning element comprises a polymer.

3. The method of claim 1, wherein the detecting fluorescence comprises detecting a change in amount of fluorescence.

4. The method of claim 1, wherein the microorganism is a biological contaminant.

5. The method of claim 1, wherein the at least one enzyme is selected from β-glucuronidase and β-galactosidase.

6. The method of claim 4, wherein the microorganism is selected from *E. coli* and total coliform.

7. The method of claim 1, wherein the at least one substrate is selected from pyrene-β-D-glucuronide, anthracene-β-D- glucuronide, pyrromethene-β-D-glucuronide, pyrene-β-D-galactopyranoside, and anthracene-β-D-galactopyranoside.

8. The method of claim 1, wherein the sample is selected from water, a biological sample, food, and soil.

9. The method of claim 1, further comprising combining the sample and the at least one substrate in a cartridge comprising the partitioning element.

10. The method of claim 2, wherein the partitioning element comprises a hydrophobic polymer.

11. The method of claim 2, wherein the polymer comprises polydimethylsiloxane (PDMS).

12. The method of claim 1, further comprising using an excitation light source to irradiate the biological molecule or the at least one substrate partitioned into the partitioning element.

13. The method of claim 1, wherein the partitioning element allows partitioning of substantially only the biological molecule thereinto.

14. The method of claim 1, wherein $K_{fs}$ is greater than one.

15. The method of claim 8, wherein the sample is a water sample.

\* \* \* \* \*